(12) United States Patent
Lee et al.

(10) Patent No.: US 9,186,322 B2
(45) Date of Patent: Nov. 17, 2015

(54) PLATINUM AGGREGATES AND PROCESS FOR PRODUCING THE SAME

(75) Inventors: Jin K. Lee, Belle Mead, NJ (US); Brian S. Miller, Mercerville, NJ (US); Fangjun Wu, Livingston, NJ (US); Lawrence T. Boni, Monmouth Junction, NJ (US); Vladimir Malinin, Plainsboro, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 764 days.

(21) Appl. No.: 12/027,752

(22) Filed: Feb. 7, 2008

(65) Prior Publication Data

US 2008/0187578 A1 Aug. 7, 2008

Related U.S. Application Data

(63) Continuation-in-part of application No. 10/634,144, filed on Aug. 4, 2003, now abandoned.

(60) Provisional application No. 60/400,875, filed on Aug. 2, 2002.

(51) Int. Cl.
*A61K 9/127* (2006.01)
*A61K 9/00* (2006.01)
(Continued)

(52) U.S. Cl.
CPC ............... *A61K 9/0078* (2013.01); *A61K 9/127* (2013.01); *A61K 9/1277* (2013.01); *A61K 31/28* (2013.01); *A61K 33/24* (2013.01); *A61K 47/48053* (2013.01); *A61K 47/48123* (2013.01)

(58) Field of Classification Search
CPC ....................................................... A61K 9/127
USPC .......................................................... 424/450
See application file for complete search history.

(56) References Cited

U.S. PATENT DOCUMENTS

| | | |
|---|---|---|
| 4,451,447 A | 5/1984 | Kaplan et al. |
| 4,590,001 A | 5/1986 | Stjernholm |

(Continued)

FOREIGN PATENT DOCUMENTS

| | | |
|---|---|---|
| CN | 1088777 A | 7/1994 |
| EP | 0 551 169 | 7/1993 |

(Continued)

OTHER PUBLICATIONS

Burger et al., "Nanocapsules: lipid-coated aggregates of cisplatin with high cytotoxity," Nature Medicine, 8(1):81-84 (2002).

(Continued)

*Primary Examiner* — Gollamudi Kishore
(74) *Attorney, Agent, or Firm* — Cooley LLP

(57) ABSTRACT

One aspect of the disclosure relates to a new form of lipid-complexed active platinum compound, which allows for high concentrations of platinum compound in the composition. For example, the concentration of cisplatin in the composition is higher at room temperature, e.g., about greater than 1.2 mg/mL, compared to 1 mg/mL in aqueous solution. In one embodiment, the present invention is directed to a composition comprising a lipid-complexed active platinum compound, wherein the complex has a lipid to drug (L/D) ratio of less than about 1 by weight, e.g. about 0.10 to 1, wherein the lipid-complexed active platinum compound comprises at least one lipid and at least one active platinum compound. In other embodiments, wherein lipid-complexed active platinum compound has an average volume-weighted diameter of about 0.5 to about 20 microns. In still other embodiments, the composition further comprises a liposome. The liposome may comprise at least one lipid, and may further comprise at least one active platinum compound. The disclosure also relates to a pharmaceutical formulation comprising a lipid complexed active platinum compound and a pharmaceutically acceptable carrier or diluent. The pharmaceutical formulation may be formulated for inhalation or injection.

17 Claims, 14 Drawing Sheets

(51) Int. Cl.
*A61K 31/28* (2006.01)
*A61K 33/24* (2006.01)
*A61K 47/48* (2006.01)

(56) References Cited

U.S. PATENT DOCUMENTS

| | | | |
|---|---|---|---|
| 4,767,874 A | | 8/1988 | Shima et al. |
| RE33,071 E | | 9/1989 | Stjernholm |
| 4,889,724 A | | 12/1989 | Kasan et al. |
| 4,981,692 A | | 1/1991 | Popescu et al. |
| 5,013,556 A | | 5/1991 | Woodle et al. |
| 5,019,369 A | | 5/1991 | Presant et al. |
| 5,049,388 A | | 9/1991 | Knight et al. |
| 5,077,057 A | * | 12/1991 | Szoka, Jr. ............ 424/1.21 |
| 5,094,854 A | | 3/1992 | Ogawa et al. |
| 5,117,022 A | | 5/1992 | Khokhar et al. |
| 5,141,751 A | * | 8/1992 | Tomikawa et al. ........... 424/450 |
| 5,186,940 A | | 2/1993 | Khokhar et al. |
| 5,264,221 A | | 11/1993 | Tagawa et al. |
| 5,320,906 A | | 6/1994 | Eley et al. |
| 5,567,434 A | | 10/1996 | Szoka, Jr. |
| 5,616,334 A | | 4/1997 | Janoff et al. |
| 5,641,662 A | | 6/1997 | Debs et al. |
| 5,665,383 A | | 9/1997 | Grinstaff et al. |
| 5,756,353 A | | 5/1998 | Debs |
| 5,780,054 A | | 7/1998 | Tardi et al. |
| 5,795,589 A | | 8/1998 | Mayer et al. |
| 5,945,122 A | | 8/1999 | Abra et al. |
| 5,997,899 A | | 12/1999 | Ye et al. |
| 6,090,407 A | | 7/2000 | Knight et al. |
| 6,126,966 A | * | 10/2000 | Abra et al. ............ 424/450 |
| 6,147,060 A | | 11/2000 | Zasloff et al. |
| 6,211,388 B1 | | 4/2001 | Tsuji et al. |
| 6,221,388 B1 | | 4/2001 | Hersch et al. |
| 6,274,115 B1 | * | 8/2001 | Presant et al. ............ 424/1.21 |
| 6,352,996 B1 | | 3/2002 | Cao et al. |
| 6,419,901 B2 | | 7/2002 | Placke et al. |
| 6,440,393 B1 | | 8/2002 | Waldrep et al. |
| 6,451,784 B1 | | 9/2002 | Placke et al. |
| 6,511,676 B1 | * | 1/2003 | Boulikas ............ 424/450 |
| 6,599,912 B1 | | 7/2003 | Au et al. |
| 6,669,958 B1 | | 12/2003 | Trager et al. |
| 6,723,338 B1 | | 4/2004 | Sarris et al. |
| 6,726,925 B1 | | 4/2004 | Needham |
| 6,787,132 B1 | | 9/2004 | Gabizon et al. |
| 6,793,912 B2 | | 9/2004 | Pilkiewicz et al. |
| 6,852,334 B1 | | 2/2005 | Cullis et al. |
| 7,025,988 B2 | | 4/2006 | Zadi |
| 7,063,860 B2 | | 6/2006 | Chancellor et al. |
| 2001/0010822 A1 | * | 8/2001 | Cherian ............ 424/400 |
| 2002/0009415 A1 | | 1/2002 | Batich et al. |
| 2002/0012998 A1 | * | 1/2002 | Gonda et al. ............ 435/458 |
| 2002/0110586 A1 | | 8/2002 | Madden et al. |
| 2002/0182248 A1 | | 12/2002 | Yamauchi et al. |
| 2002/0187105 A1 | | 12/2002 | Zou et al. |
| 2003/0059375 A1 | | 3/2003 | Perez-Soler et al. |
| 2003/0059402 A1 | * | 3/2003 | Jin et al. ............ 424/93.2 |
| 2003/0099718 A1 | | 5/2003 | Burrell et al. |
| 2003/0185879 A1 | * | 10/2003 | Boulikas ............ 424/450 |
| 2004/0101553 A1 | | 5/2004 | Lee et al. |
| 2004/0156888 A1 | | 8/2004 | Jensen et al. |
| 2004/0170678 A1 | * | 9/2004 | Madden et al. ............ 424/450 |
| 2005/0037341 A1 | | 2/2005 | Dierynck et al. |
| 2005/0074499 A1 | | 4/2005 | Tagawa et al. |
| 2005/0207987 A1 | | 9/2005 | Speirs et al. |

FOREIGN PATENT DOCUMENTS

| | | |
|---|---|---|
| EP | 0 719 546 | 7/1996 |
| JP | 2001-501173 | 1/2001 |
| WO | WO-98/07409 | 2/1998 |
| WO | WO-98/24425 | 6/1998 |
| WO | WO-98/29110 | 7/1998 |
| WO | WO-99/15153 | 4/1999 |
| WO | WO-00/27359 | 5/2000 |
| WO | WO-01/32139 | 5/2001 |
| WO | WO-01/34130 | 5/2001 |
| WO | WO-03/015707 | 2/2003 |
| WO | WO-2004/054499 | 7/2004 |
| WO | WO-2005/037341 | 4/2005 |
| WO | WO-2005/089448 | 9/2005 |

OTHER PUBLICATIONS

Boulikas, T., "Low toxicity and anticancer activity of a novel liposomal cisplatin (Lipoplatin) in mouse xenografts," Oncology Reports, 12:3-12 (2004).
Chi et al., "Elimination of Dose Limiting Toxicities of Cisplatin, 5-Fluorouracil, and Leucovorin Using a Weekly 24-Hour Infusion Schedule for the Treatment of Patients with Nasopharyngeal Carcinoma," Cancer, 76(11):2186-2192 (1995).
Cisplatin Injection, Drug Information Label, Jun. 2004.
Comis, R.L., "Carboplatin in the treatment of non-small cell long cancer: a review," Oncology, 50(2):37-41 (1993).
Comis, Robert L., "Carboplatin in the Treatment of Non-Small Cell Lung Cancer: A Review," Oncology, 50(Suppl 2):37-41 (1993).
Devarajan et al., "Low Renal Toxicity of Lipoplatin Compared to Cisplatin in Animals," Anticancer Research, 24:2193-2200 (2004).
Embree et al., "Chromatographic Analysis and Pharmacokinetics of Liposome-Encapsulated Doxorubicin in Non-Small-Cell Lung Cancer Patients," Journal of Pharmaceutical Sciences, 82(6):627-634 (1993).
Fujita et al., "Respiratory failure due to pulmonary lymphangitis carcinomatosis," Chest, 103(3):967-968 (1993).
Hoffman et al., "Lung Cancer," The Lancet, 355:479-485 (2000).
Hojo et al., "A case of adenocarcinoma of lung cancer with multiple brain metastasis and lymphangitis carcinomatosa responding well to chemotherapy with carboplatin, etoposide and ifosfamide," Gan to Kagaku, 19(14):2403-6 (1992) Abstract.
Kinoshita, A., "Investigation of Cisplatin Inhalation Chemotherapy Effects on Mice after Air Passage Implantation of FM3A Cells," Journal of Japan Society for Cancer Therapy, 28(4):705-715 (1993).
Knight et al., "Anti-Cancer Activity of 9-Nitrocamptothecin Liposome Aerosol in Mice," Transactions of the American Clinical and Climatological Association, vol. III, pp. 135-145 (2000).
Koshkina et al., "9-Nitrocamptothecin Liposome Aerosol Treatment of Melanoma and Osteosarcoma Lung Metastases in Mice," Clinical Cancer Research, 6(7):2876-2880 (2000).
Lehninger et al., Principles of Biochemistry, Worth Publishers: New York, pp. 111-114, 134-135, 240-245, 247, 249-252, 254, 256-259, and 262.
Leighl et al., "A Phase I Study of Pegylated Liposomal Doxorubicin Hydrochloride (Caelyx™) in Combination with Cyclophosphamide and Vincristine as Second-Line Treatment of Patients with Small-Cell Lung Cancer," Clinical Lung Cancer, 5(2):107-112 (2003).
Liams et al., "Clinical Features of Patients with Stage IIIB and IV Bronchioloaleolar Carcinoma of the Lung," Cancer, 86:1165-1173 (1999).
Okuyama et al., "Reinforcing Aerosol Cisplatin for Radiotherapy of Laryngeal Cancer," Tohoku Journal of Experimental Medicine, 169(3):253-255 (1993).
Platinol®-AQ (cisplatin injection), Drug Information Label, 1999.
Poster and Oral Presentation: Chou et al., "Phase Ib/IIa study of sustained release lipid inhalation targeting cisplatin by inhalation in the treatment of patients with relapsed/progressive osteosarcoma metastic to the lung," Journal of Clinical Oncology, 2007 ACSO Annual Meeting Proceedings, Part I, 25(18S).
Poster: Perkins et al., "An Inhalation Formulation of Liposomal Cisplatin (SLIT™Cisplatin) for Treatment of Lung Cancer," Lipids, Liposomes & Biomembranes 2005: New Technologies Jul. 26-30, University of British Columbia, Vancouver, Canada, p. 78.
Poster: Wittgen et al., "Phase I study of aerolized SLIT cisplatin in the treatment of patients with carcinoma of the lung," Journal of Clinical Oncology, 2006 ASCO Annual Meeting Proceedings, Part I, 24(18S).
Poster: Zou et al., "Pharmacokinetics and organ distribution of liposomal cisplatin administered intravenously and intraperitoneally," Proceedings American Association Cancer Research 2005: 45, abs LB-268.

(56) References Cited

OTHER PUBLICATIONS

Schwartsmann et al., "A Phase I Trial of Cisplatin Plus Decitabine, a New DNA-Hypomethylating Agent, in Patients with Advanced Solid Tumors and a Follow-Up Early Phase II Evaluation in Patients with Inoperable Non-Small Cell Lung Cancer," Investigational New Drugs, 18(1):83-91 (2000).

Stathopoulos et al., "Paclitaxel combined with cis-platin as second-line treatment in patients with advanced non-small cell lung cancers refractory to cis-platin," Oncology Reports, 6:797-800 (1999).

Stathopoulos et al., "Pharmacokinetics and adverse reactions of a new liposomal cisplatin (Lipoplatin): Phase I study," Oncology Reports, 13:589-595 (2005).

Steerenberg et al., "Liposomes as Drug Carrier System for cis-diamminedichloroplatinum (II)," Cancer Chemother. Pharmacol., 21:299-307 (1998).

Vokes et al., "A Phase I Study of STEALTH Cisplatin (SPI-77) and Vinorelbine in Patients with Advanced Non-Small-Cell Lung Cancer," Clinical Lung Cancer, 2(2):128-132 (2000).

Wittgen et al., "Assessing a System to Capture Stray Aerosol during Inhalation of Nebulized Liposomal Cisplatin," Journal of Aerosol Medicine, 19(3):385-391 (2006).

Wittgen et al., "Phase I Study of Aerosolized SLIT Cisplatin in the Treatment of Patients with Carcinoma of the Lung," Clin. Cancer Res., 13(8):2414-2421 (2007).

\* cited by examiner

PLATINUM AGGREGATES AND PROCESS FOR PRODUCING THE SAME

RELATED APPLICATIONS

This application is a continuation-in-part of U.S. application Ser. No. 10/634,144, filed on Aug. 4, 2003, filed, which claims priority to U.S. Provisional Application 60/400,875, filed on Aug. 2, 2002, both of which are herein incorporated by reference.

BACKGROUND OF THE INVENTION

Liposomes and lipid complexes have been long recognized as drug delivery systems which can improve therapeutic and diagnostic effectiveness of many bioactive agents and contrast agents. Experiments with a number of different antibiotics and X-ray contrast agents have shown that better therapeutic activity or better contrast with a higher level of safety can be achieved by encapsulating bioactive agents and contrast agents with liposomes or lipid complexes. Research on liposomes and lipid complexes as encapsulating systems for bioactive agents has revealed that a successful development and commercialization of such products requires reproducible methods of large scale production of lipid vesicles with suitable characteristics. Consequently, workers have searched for methods which consistently produce liposomes or lipid complexes of the required size and concentration, size distribution and, importantly, entrapping capacity, with flexible lipid composition requirements. Such methods seek to provide liposomes or lipid complexes with consistent active substance to lipid ratio while respecting currently accepted good manufacturing practices for pharmaceutical products.

Conventional liposome and lipid complex preparation methods include a number of steps in which the bilayer-forming components (for example, phospholipids or mixtures of phospholipids with other lipids e.g., cholesterol) are dissolved in a volatile organic solvent or solvent mixture in a round bottom flask followed by evaporation of the solvent under conditions, such as temperature and pressure, which will prevent phase separation. Upon solvent removal a dry lipid mixture, usually in form of a film deposit on the walls of the reactor, is hydrated with an aqueous medium which may contain dissolved buffers, salts, conditioning agents and an active substance to be entrapped. Liposomes or lipid complexes form in the hydration step such that a proportion of the aqueous medium becomes encapsulated in the liposomes. The hydration can be performed with or without energizing the solution by means of stirring, sonication or microfluidization or with subsequent extrusion through one or more filters, such as polycarbonate filters. The free non-encapsulated active substance can be separated for recovery and the product is filtered, sterilized, optionally lyophilized, and packaged.

Other methods of making liposomes or lipid complexes involving injection of organic solutions of lipids into an aqueous medium with continuous removal of solvent, use of spray drying, lyophilization, microemulsification and microfluidization, and the like have been proposed in a number of publications or patents. Such patents include, for example, U.S. Pat. No. 4,529,561 and U.S. Pat. No. 4,572,425.

Cisplatin—cis-diamine-dichloroplatinum (II)—is one of the more effective anti-tumor agents used in the systemic treatment of cancers. This chemotherapeutic drug is highly effective in the treatment of tumor models in laboratory animals and in human tumors, such as endometrial, bladder, ovarian and testicular neoplasms, as well as squamous cell carcinoma of the head and neck (Sur, et al., 1983 Oncology 40(5): 372-376; Steerenberg, et al., 1988 Cancer Chemother Pharmacol. 21(4): 299-307). Cisplatin is also used extensively in the treatment of lung carcinoma, both small cell lung carcinoma (SCLC) and non-small cell lung carcinoma (NSCLC) (Schiller et al., 2001 Oncology 61(Suppl 1): 3-13). Other active platinum compounds (defined below) are useful in cancer treatment.

Like other cancer chemotherapeutic agents, active platinum compounds such as cisplatin are typically highly toxic. The main disadvantages of cisplatin are its extreme nephrotoxicity, which is the main dose-limiting factor, its rapid excretion via the kidneys, with a circulation half life of only a few minutes, and its strong affinity to plasma proteins (Freise, et al., 1982 Arch Int Pharmacodyn Ther. 258(2): 180-192).

Attempts to minimize the toxicity of active platinum compounds have included combination chemotherapy, synthesis of analogues (Prestayko et al., 1979 Cancer Treat Rev. 6(1): 17-39; Weiss, et al., 1993 Drugs. 46(3): 360-377), immunotherapy and entrapment in liposomes (Sur, et al., 1983; Weiss, et al., 1993). It has been reported that antineoplastic agents, including cisplatin, entrapped in liposomes have a reduced toxicity, relative to the agent in free form, while retaining antitumor activity (Steerenberg, et al., 1987; Weiss, et al., 1993).

Cisplatin, however, is difficult to efficiently entrap in liposomes or lipid complexes because of its low aqueous solubility, approximately 1.0 mg/mL at room temperature, and low lipophilicity, both of which properties contribute to a low cisplatin/lipid ratio.

Liposomes and lipid complexes containing cisplatin suffer from another problem—stability of the composition. In particular, maintenance of bioactive agent potency and retention of the bioactive agent in the liposome during storage are recognized problems (Freise, et al., 1982; Gondal, et al., 1993; Potkul, et al., 1991 Am J Obstet Gynecol. 164(2): 652-658; Steerenberg, et al., 1988; Weiss, et al., 1993) and a limited shelf life of liposomes containing cisplatin, on the order of several weeks at 4° C., has been reported (Gondal, et al., 1993 Eur J. Cancer. 29A(1): 1536-1542; Potkul, et al., 1991).

SUMMARY OF THE INVENTION

Provided, among other things, is a new form of lipid-complexed active platinum compound, which allows for high concentrations of platinum compound in a composition. For example, the concentration of cisplatin in the composition is higher at room temperature, e.g., about greater than 1.2 mg/mL, compared to 1 mg/mL in aqueous solution. The lipid-complexed active platinum compound is stable over long periods of time. For example, the lipid-complexed active platinum compound is stable for more than one year.

In one embodiment, the present invention is directed to a composition comprising a lipid-complexed active platinum compound, wherein the complex has a lipid to drug (L/D) ratio of less than about 1 by weight, e.g. about 0.10 to 1, wherein the lipid-complexed active platinum compound comprises at least one lipid and at least one active platinum compound.

In some embodiments, wherein lipid-complexed active platinum compound has an average volume-weighted diameter of about 0.5 to about 20 microns.

In some embodiments, the composition further comprises a liposome. The liposome may comprise at least one lipid, and may further comprise at least one active platinum compound.

In some embodiments, the present invention relates to a pharmaceutical formulation comprising a lipid complexed active platinum compound and a pharmaceutically acceptable carrier or diluent. The pharmaceutical formulation may be formulated for inhalation or injection.

DETAILED DESCRIPTION OF THE INVENTION

Figure 1A:
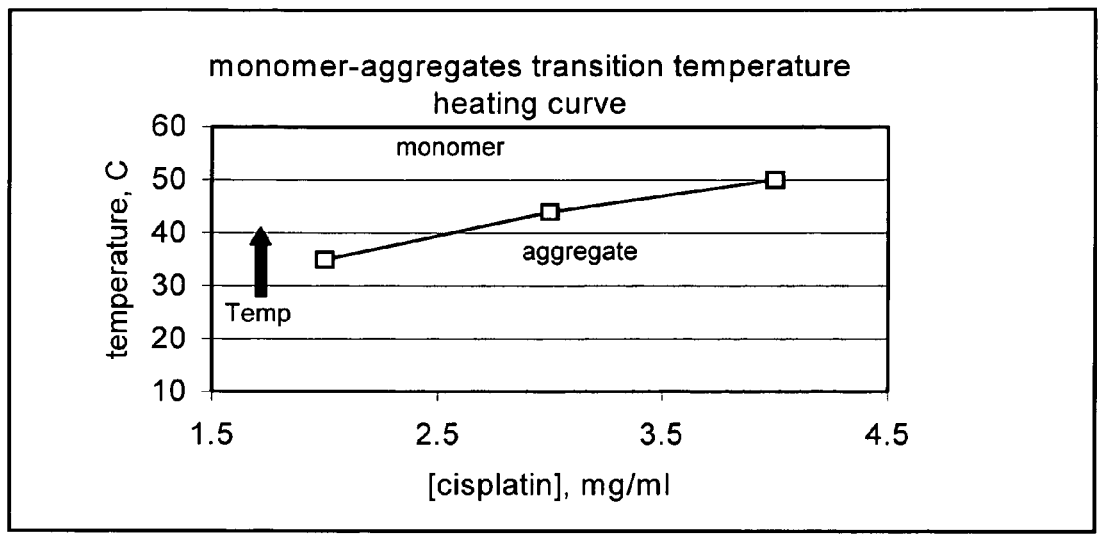
FIG. 1(A) depicts a graph of the transition temperature for dissolution and precipitation of cisplatin in aqueous solution as a function of cisplatin concentration during heating.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e. to at least one) of the grammatical object of the article. By way of example, "an element" means one element or more than one element.

The term "bioavailable" is art-recognized and refers to a form of the subject invention that allows for it, or a portion of the amount administered, to be absorbed by, incorporated to, or otherwise physiologically available to a subject or patient to whom it is administered.

The terms "comprise" and "comprising" are used in the inclusive, open sense, meaning that additional elements may be included.

The term "including" is used herein to mean "including but not limited to". "Including" and "including but not limited to" are used interchangeably.

The term "mammal" is known in the art, and exemplary mammals include humans, primates, bovines, porcines, canines, felines, and rodents (e.g., mice and rats).

A "patient," "subject" or "host" to be treated by the subject method may mean either a human or non-human animal.

The term "pharmaceutically-acceptable salts" is art-recognized and refers to the relatively non-toxic, inorganic and organic acid addition salts of compounds, including, for example, those contained in compositions of the present invention.

The term "treating" is art-recognized and refers to curing as well as ameliorating at least one symptom of any condition or disorder.

"Solvent infusion" is a process that includes dissolving one or more lipids in a small, preferably minimal, amount of a process compatible solvent to form a lipid suspension or solution (preferably a solution) and then injecting the solution into an aqueous medium containing bioactive agents. Typically a process compatible solvent is one that can be washed away in a aqueous process such as dialysis. The composition that is cool/warm cycled is preferably formed by solvent infusion, with ethanol infusion being preferred. Alcohols are preferred as solvents. "Ethanol infusion," a type of solvent infusion, is a process that includes dissolving one or more lipids in a small, preferably minimal, amount of ethanol to form a lipid solution and then injecting the solution into an aqueous medium containing bioactive agents. A "small" amount of solvent is an amount compatible with forming liposomes or lipid complexes in the infusion process.

A "hydrophobic matrix carrying system" is the lipid/solvent mixture produced by the solvent infusion process described above.

The present invention relates to a new form of lipid-complexed active platinum compound, which allows for high concentrations of platinum compound in the composition. For example, the room temperature concentration of cisplatin in the composition is higher, e.g., greater than 1.2 mg/mL, compared to 1 mg/mL of active platinum compound aqueous solution. In some embodiments, the lipid complexed active platinum compound comprises a lipid bilayer, where the lipid bilayer encapsulates or entraps the platinum compound.

In some embodiments, the composition comprises a lipid-complexed active platinum compound, wherein the complex has a lipid to drug ratio of less than about 1 by weight. For example the L/D ratio can be about 0.10 to 1 by weight, wherein the lipid-complexed active platinum compound comprises at least one lipid and at least one active platinum compound. In some embodiments, the lipid to drug ratio is about 0.10 to about 0.50 by weight. In some embodiments, the lipid to drug ratio is about 0.15 to about 0.45 by weight, and in other embodiments, the lipid to drug ratio is about 0.20 to 0.40 by weight. In some embodiments, the lipid to drug ratio is about 0.2 by weight.

The lipid-complexed active platinum compound may have an average volume-weighted diameter of about 0.5 to about 20 microns. In some embodiments, the average volume-weighted diameter is about 1 to about 15 microns, or about 2 to about 10 microns. In other embodiments, the average volume-weighted diameter is about 3, 4, 5, or 6 microns.

In some embodiments, the concentration of the active platinum compound in the composition is greater than about 1.2 mg/mL, for example about 1.2 to about 20 mg/mL. In other embodiments, the concentration of the active platinum compound is about 1.2 to 10 mg/mL, about 1.5 to about 5 mg/mL, about 2.0 to about 4 mg/mL, or about 3.0 to 2.5 mg/mL. In other embodiments, the concentration is about 2, about 3, or about 5 mg/mL.

In some embodiments, the composition comprising the lipid-complexed active platinum compound further comprises a liposome. As explained in greater detail in the examples below, the liposome comprises at least one lipid. The lipid may be the same as or different from the lipid in the lipid-complexed active platinum compound. In some embodiments, the liposome further comprises an active platinum compound, wherein the active platinum compound can be the same as or different from the active platinum compound of the lipid-complexed active platinum compound. The active platinum compound may be entrapped in the liposome.

In some embodiments, the liposomes have an average diameter of about 0.1 to about 1 micron, 0.1 to about 0.5 microns, about 0.2 to about 0.5 microns, or about 0.2 to about 0.3 microns.

When the lipid composition further comprises a liposome, the lipid-complexed active platinum compound may contain about 70 to about 100% of the total active platinum compound in the composition. In other embodiments, the lipid-complexed active platinum compound contains about 75 to about 99%, about 75 to about 95%, or about 80 to about 90% of the total active platinum compound in the composition. In some embodiments, the liposome contains about 0 to about 30% of the total active platinum compound in the composition. In other embodiments, the liposome may contain about 0.5 to about 25%, about 1 to about 20%, or about 5 to 10% of the total active platinum compound.

When the composition further comprises a liposome, the lipid-complexed active platinum compound may contain about 0.1 to about 5% of the total lipid in the composition. In some embodiments, the lipid-complexed active platinum compound contains about 0.25 to about 3%, or about 0.5 to about 2% of the total lipid. In some embodiments, the liposome contains about 75 to about 99.5%, about 80 to about 95%, or about 85 to about 95% of the total lipid in the composition.

When present in the composition, the liposome may have a lipid to active platinum compound ratio of about 100:1 to about 400:1 by weight. In other embodiments, the lipid to active platinum compound ratio of the liposome is about 200:1 to about 400:1, about 200: to about 300:1 about 250:1 to 300:1 or about 250:1 by weight.

In some embodiments, the composition comprising a lipid-complexed active platinum compound and a liposome has an active platinum compound concentration of greater than about 1.2 mg/mL, for example, the concentration may be about 1.2 to about 20 mg/mL, about 1.2 to about 10 mg/mL, about 1.5 to about 5 mg/mL, about 2.0 to about 4 mg/mL, or about 3.0 to about 2.5 mg/mL. In other embodiments, the concentration is about 2, about 3, or about 5 mg/mL.

An "active platinum" compound is a compound containing coordinated platinum and having antineoplastic activity. Additional active platinum compounds include, for example, carboplatin and DACH-platinum compounds such as oxaliplatin. In certain embodiments, the active platinum compounds in the composition is selected from the group consisting of cisplatin, carboplatin, oxaliplatin, iproplatin, tetraplatin, transplatin, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)) and JM335 (trans-amminedichloro(cyclohexylamine)dihydroxoplatinum(IV)). In some embodiments, the active platinum compound is cisplatin.

In certain embodiments, the active platinum compound is selected from the group consisting of cisplatin, carboplatin, oxaliplatin, iproplatin, tetraplatin, transplatin, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)) and JM335 (trans-amminedichloro(cyclohexylamine)dihydroxoplatinum(IV)). In some embodiments, the active platinum compound is cisplatin, transplatin, carboplatin, or oxaliplatin, while in other embodiments, the active platinum compound is cisplatin.

The lipids used in the present invention can be synthetic, semi-synthetic or naturally-occurring lipids, including phospholipids, tocopherols, sterols, fatty acids, glycolipids, negatively-charged lipids, cationic lipids. In terms of phospholipids, they can include such lipids as egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidyl choline (SPC); SPG, SPS, SPI, SPE, and SPA; the hydrogenated egg and soya counterparts (e.g., HEPC, HSPC), stearically modified phosphatidylethanolamines, cholesterol derivatives, carotinoids, other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. In particular, the compositions of the formulations can include DPPC, a major constituent of naturally-occurring lung surfactant. Other examples include dimyristoylphosphatidycholine (DMPC) and dimyristoylphosphatidylglycerol (DMPG) dipalmitoylphosphatidcholine (DPPC and dipalmitoylphosphatidylglycerol (DPPG) distearoylphosphatidylcholine (DSPC and distearoylphosphatidylglycerol (DSPG), dioleylphosphatidyl-ethanolamine (DOPE) and mixed phospholipids like palmitoylstearoylphosphatidylcholine (PSPC) and palmitoylstearolphosphatidylglycerol (PSPG), triacylglycerol, diacylglycerol, seranide, sphingosine, sphingomyelin and single acylated phospholipids like mono-oleoyl-phosphatidylethanolaniine (MOPE).

In some embodiments, the lipid complexed active platinum compound comprises a neutral phospholipid, such as a phosphatidyl choline. In other embodiments, the phosphatidyl choline is DPPC.

In some embodiments, the lipid complexed active platinum compound further comprises a sterol. In some embodiments, the sterol is cholesterol.

Negatively charged lipids include PGs, PAs, PSs and PIs. In some embodiments, the lipid complexed active platinum compound does not comprise a phosphatidyl serine (PS). In some embodiments, the lipid-complexed active platinum compound does not comprise a PG, PA, PS or PI. In other embodiments, the lipid-complexed active platinum compound is substantially free of negatively charged phospholipids. In some embodiments, the lipid-complexed active platinum compound does not comprise any negatively charged phospholipids.

In some embodiments, the lipid complexed active platinum compound comprises DPPC and cholesterol in a ratio of about 1:1 to about 5:1 by weight. In other embodiments, the lipid complexed active platinum compound comprises DPPC and cholesterol in a ratio of about 2:1 to about 4:1 by weight. In some embodiments, the lipid complexed active platinum compound comprises DPPC and cholesterol in a ratio of about 2.25:1 by weight.

Another aspect of the invention relates to pharmaceutical formulations comprising any one of the aforementioned compositions and a pharmaceutically acceptable carrier or diluent. The pharmaceutical formulation of the lipid complexed active platinum compound may be comprised of an aqueous dispersion of liposomes. The formulation may contain lipid excipients to form the liposomes, and salts/buffers to provide the appropriate osmolarity and pH. The pharmaceutical excipient may be a liquid, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient. Suitable excipients include trehalose, raffinose, mannitol, sucrose, leucine, trileucine, and calcium chloride. Examples of other suitable excipients include (1) sugars, such as lactose, and glucose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In some embodiments, the pharmaceutical formulation is adapted for inhalation by or injection into a patient.

The process for producing this active platinum compound formulation can comprise mixing an active platinum compound with an appropriate hydrophobic matrix and subjecting the mixture to one or more cycles of establishing two separate temperatures. For example, the process comprises the steps of: (a) combining an active platinum compound and a hydrophobic matrix carrying system; (b) establishing the mixture at a first temperature; and (c) thereafter establishing the mixture at a second temperature, which second temperature is cooler than the first temperature. Step (b) is typically effected with heating, while step (c) is typically effected with cooling. In alternative embodiments, the cycles are counted beginning with the cooler step, transitioning to the warmer step, and cycling the two steps. The process can comprise sequentially repeating the steps (b) and (c) for a total of two or three or more cycles. The active platinum compound solution can be produced by dissolving active platinum compound in a saline solution to form a platinum solution. The hydrophobic matrix carrying system favorably comprises liposome or lipid complex-forming lipids. The process for making a platinum aggregate can further comprise, after all of steps (b) and steps (c) have been completed: (d) removing un-entrapped active platinum compound by filtering through a membrane having a molecular weight cut-off selected to retain desired liposomes or lipid complexes and adding a liposome or lipid complex compatible liquid to wash out un-entrapped active platinum compound.

Cisplatin, for example, forms large crystalline aggregates in aqueous solution with a crystal diameter of greater than a few microns. In the presence of an amphipathic matrix system, such as a lipid bilayer, small cisplatin aggregates form. For example, the aggregates may be formed in the hydrocarbon core region of a lipid bilayer or be formed such that a lipid bilayer surrounds the aggregate. During the warming cycle of the process, it is believed that cisplatin is returned to solution at a greater rate in aqueous regions of the process mixture than in the bilayers. As a result of applying more than one cool/warm cycle, cisplatin accumulates further in the core region of the lipid bilayers or within the lipid bilayer. Without limiting the invention to the proposed theory, experimentation indicates that the cisplatin aggregates cause the immediate surroundings of the interfacial bilayer region to be more hydrophobic and compact. This results in a high level of entrapment of active platinum compound as cooling and warming cycles are repeated.

The resulting formulation has a markedly high entrapment percentage. The entrapment has been shown, in some cases, to reach almost 92%. This amount is far higher than the most efficient entrapment expected from a conventional aqueous entrapment which is approximately 2-10% entrapment. This efficiency of the present invention is demonstrated in example 3.

In one embodiment, the process comprises combining the bioactive agent with a hydrophobic matrix carrying system and cycling the solution between a warmer and a cooler temperature. Preferably the cycling is performed more than one time. More preferably the step is performed two or more times, or three or more times. The cooler temperature portion of cycle can, for example, use a temperature of about 35° C. or less, 25° C. or less, 20° C. or less, 15° C. or less, 10° C. or less, or 5° C. or less. In some embodiments, the temperature is about −25° Celsius to about 35° Celsius, about −5 to about 25° C., about −5 and about 20° C., about −5 and about 10° C., about −5 and about 5° C., or about 1 and about 5° C.

In some embodiments, the warming step temperature is 50° Celsius or higher. The temperatures can also be selected to be below and above the transition temperature for a lipid in the lipid composition. In some embodiments the step of warming comprises warming the reaction vessel to about 4 to about 70° Celsius, about 45 and to about 55° Celsius. The above temperature ranges are particularly preferred for use with lipid compositions comprising predominantly diphosphatidycholine (DPPC) and cholesterol.

For manufacturing convenience, and to be sure the desired temperature is established, the cooler and warmer steps can be maintained for a period of time, such as approximately form 5 to 300 minutes or 30 to 60 minutes.

Another way to consider the temperature cycling is in terms of the temperature differential between the warming and cooling steps of the cycle. This temperature differential can be, for example, about 25° Celsius or more, such as a differential from about 25 to about 70° Celsius, or a differential of about 40 to about 55° Celsius.

The temperatures of the warming and cooling steps are selected on the basis of increasing entrapment of active platinum compound. Without being limited by any particular theory, it is believed that it is useful to select an upper temperature effective substantially increase the solubility of active platinum compound in the process mixture. During repetitive cooling/heating, bioactive agents are solubilized and crystallized repetitively. As soluble drug is cooled, some portion enters complexes with the lipid while the remainder precipitates. On subsequent heating, unencapsulated bioactive agent that is crystallized becomes soluble again. Importantly, active platinum compound that has been encapsulated in the lipid complex substantially stays in the lipid complex during the heating and cooling cycling (e.g. it leaks at such a slow rate that no appreciable amount leaves the lipid complex during the heating phase of this process).

For example, as the temperature is increased during the warming step of the cycle, the active platinum compound, such as cisplatin, dissolves. During the cooling step, the cisplatin in the aqueous phase precipitates out of solution to a greater extent that the cisplatin associated with the lipid bilayers, thereby increasing the amount of lipid-associated cisplatin with each heating and cooling cycle. Additionally, solubility of cisplatin is highly temperature-dependent. For example, FIG. 1A depicts a graph of the transition temperature of dissolved-precipitated cisplatin in aqueous solution as a function of cisplatin concentration during heating (where the cisplatin is initially in precipitated). FIG. 1C depicts a graph of the transition temperature at which aqueous cisplatin is precipitated during cooling (where the cisplatin is initially dissolved). Lowering 15° in temperature of a cisplatin solution decreases the soluble concentration by about 50%. In other words, solubility limiting concentration increases with increasing temperature by about 3% per degree increase in temperature of aqueous cisplatin. In addition, the aggregate (crystal)-to-monomer transition temperature (solubilizing temperature) is higher than the monomer-to-aggregate (crystal) transition temperature (crystallizing temperature) by about 15 to 20° C.

Figure 1B:
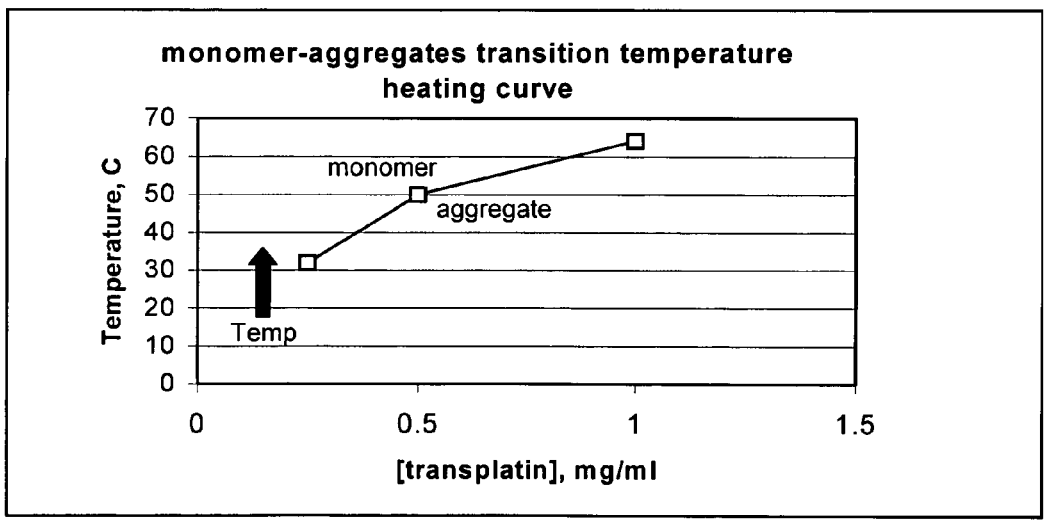
FIG. 1(B) depicts a similar graph of transplatin.
Figure 1C:
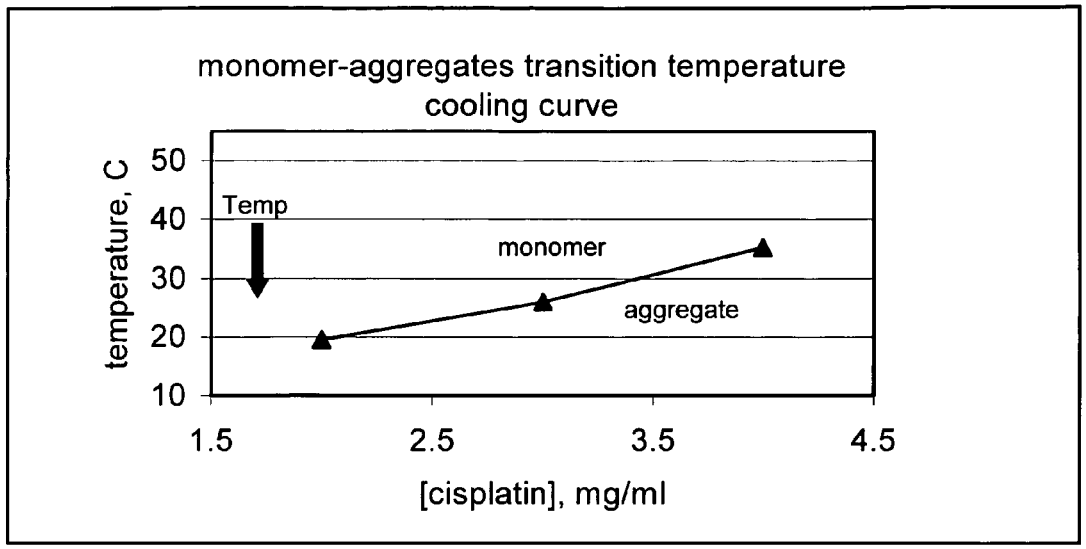
FIGS. 1(C) and 1(D) depict graphs of the transition temperature of dissolved-precipitated cisplatin in aqueous solution as a function of concentration during cooling of cisplatin and transplatin, respectively.
Figure 1D:
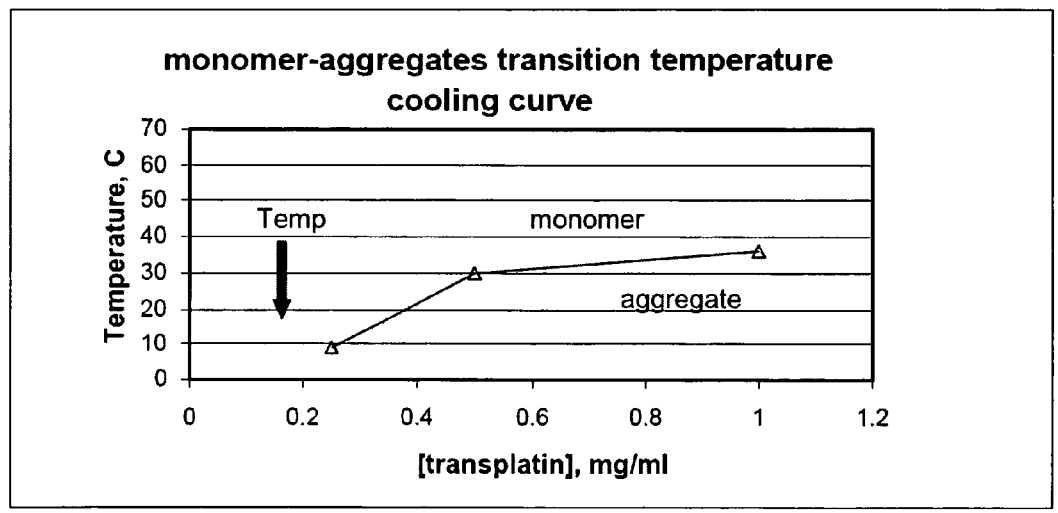

Similar graphs for another active platinum compound, transplatin, are depicted in FIGS. 1B and 1D, which show solubility properties similar to cisplatin. Transplatin solubility is poorer than cisplatin, but it is also temperature-dependent. Lowering the temperature by about 15° C. decreases the soluble concentration of transplatin by about 50%. The aggregate (crystal)-to-monomer transition temperature (solubilizing temperature) is higher than the monomer-to-aggregate (crystal) transition temperature (crystallizing temperature) by about 20 to 30° C.

Experimental results strongly indicate that the physical state of cisplatin is solid (aggregates) or lipid bound since the concentration of cisplatin is much higher than the solubility limit. Results further indicate that process does not require freezing the compositions, but that cooling to temperature higher than the freezing point of water is effective. Results further indicated that an entrapment efficiency achieved by 3-cycles was similar to that achieved by 6-cycles of cooling and warming cycles, which indicated that 3 cycles of temperature treatment was sufficient to achieve high levels of active platinum compound entrapment.

Results further indicate that the process can be scaled-up while increasing process efficiency in entrapping cisplatin. Thus, the invention further provides processes that are conducted to provide an amount adapted for total administration (in appropriate smaller volume increments) of 200 or more mLs, 400 or more mLs, or 800 or more mLs. All else being the same, it is believed that the larger production volumes generally achieve increased efficiency over smaller scale processes. While such volume is that appropriate for administration, it will be recognized that the volume can be reduced for storage.

Results further indicate that the lipid-complexed cisplatin made by the method of the invention can retain entrapped cisplatin with minimal leakage for over one year. This is a further demonstration of the uniqueness in the formulation, indicating that the cisplatin is bound within the liposome structure and not free to readily leak out.

The process of the present invention may further comprise separating the components of the product of the aforementioned process. For example, in some embodiments, the process provides both the aforementioned lipid-complexed active platinum compound and the aforementioned liposome. In certain embodiments, the portion of the product comprising the lipid-complexed active platinum compound, referred to herein as "the heavy fraction" may be separated from the portion comprising the liposome, referred to herein as "the light fraction." Methods of separating include allowing the heavy product to settle over a period of time, or centrifuging the product.

Example 1

70 mg DPPC and 28 mg cholesterol was dissolved in 1 mL ethanol and added to 10 mL of 4 mg/mL cisplatin in 0.9% saline solution.

(i) An aliquot (50%) of the sample was treated by 3 cycles of cooling to 4° C. and warming to 50° C. The aliquot, in a test tube, was cooled by refrigeration, and heated in a water bath. The resulting unentrapped cisplatin (free cisplatin) was washed by dialysis.

(ii) The remainder of the sample was not treated by temperature cycles and directly washed by dialysis.

TABLE 1

Percentage entrapment of cisplatin with and without cooling and warming cycles.

|  | Final Concentration of cisplatin, µg/mL | % Entrapment |
| --- | --- | --- |
| Lipid-complexed cisplatin without cooling and warming cycles | 56 | 1.4 |
| lipid-complexed cisplatin after cooling and warming cycles | 360 | 9.0 |

Example 2

The rigidity of a membrane bilayer in lipid-complexed cisplatin prepared with cool/warm cycling ("HLL" cisplatin or "high-load liposomal" cisplatin) as described in Example 1 was measured by fluorescence anisotropy of diphenylhexatriene (membrane probe) inserted in the hydrophobic core region of the bilayer. [Ref. Jahnig, F., 1979 *Proc. Natl. Acad. Sci. USA* 76(12): 6361.] The hydration of the bilayers was gauged by the deuterium isotope exchange effect on fluorescence intensity of TMA-DPH (trimethylamine-diphenylhexatriene). [Ref. Ho, C., Slater, S. J., and Stubbs, C. D., 1995 *Biochemistry* 34: 6188.]

TABLE 2

Degree of hydration and rigidity of liposomes, lipid-complexed cisplatin without cool/warm cycling and HLL cisplatin.

|  | Placebo (Liposomes without cisplatin) | Lipid-complexed cisplatin without cooling & warming cycles | HLL cisplatin |
| --- | --- | --- | --- |
| Degree bilayer rigidity | 0.29 | 0.29 | 0.36 |
| Degree of bilayer hydration | 1.13 | 1.15 | 1.02 |

Example 3

1.0 g DPPC and 0.4 g cholesterol were dissolved in 6 ml of ethanol. 60 mg of cisplatin was dissolved in 10 mL of 0.9% saline solution at 65° C. 1 mL of the resultant lipid mixture solution was added to 10 mL of the resultant cisplatin solution. The lipid/cisplatin suspension was cooled to approximately 4° C. and held at that temperature for 20 min. and warmed to 50° C. and held at that temperature for 20 min. Ethanol was removed by bubbling $N_2$ gas into the suspension during the warming period. The cooling and warming steps were repeated 5 further times.

TABLE 3

Entrapment of cisplatin.

| | Concentration of Total Cisplatin (mg/mL) | % Cisplatin entrapped | Drug:Lipid (by weight) |
|---|---|---|---|
| HLL Cisplatin | 5.8 | 91.6 | 1:26 |

Example 4

A cisplatin lipid formulation was prepared using phosphatidylcholine (PC) and cholesterol (in a 57:43 mol ratio). 0.55 mmoles of PC and 0.41 mmoles of cholesterol were dissolved in 2 mL ethanol and added to 20 mL of 4 mg/mL cisplatin solution. An aliquot (50%) of each sample was treated by 3 cycles of cooling and warming and then washed by dialysis. Another part of each sample was directly washed by dialysis. Entrapment was estimated from the ratio of final concentration and initial concentration.

TABLE 4

Entrapment and drug to lipid ratios for cisplatin with various phosphatidylcholines.

| | No Cooling and Warming | | | Cooling and Warming | | |
|---|---|---|---|---|---|---|
| PC | Cisplatin (mg/mL) | % Entrapment | Drug:Lipid (by weight) | Cisplatin (mg/mL) | % Entrapment | Drug:Lipid (by weight) |
| DOPC | 0.16 | 4.0 | 1:142 | 0.21 | 5.3 | 1:108 |
| EggPC | 0.09 | 2.3 | 1:247 | 0.12 | 3.0 | 1:185 |
| DMPC | 0.15 | 3.8 | 1:123 | 0.24 | 6.0 | 1:77 |
| DPPC | 0.17 | 4.3 | 1:115 | 0.85 | 21.3 | 1:23 |
| HSPC | 0.11 | 2.8 | 1:202 | 0.23 | 5.8 | 1:97 |
| DSPC | 0.10 | 2.5 | 1:184 | 0.58 | 14.5 | 1:32 |

Example 5

A lipid formulation (DPPC:cholesterol in a ratio of 5:2 w/w) was dissolved in ethanol and added to a cisplatin solution. Part of the formulation was treated by cycles of cooling to 4° Celsius and warming to 55° Celsius cycles while part was not treated thus. The lipid/cisplatin suspension was then washed by dialysis.

TABLE 5

Concentration of cisplatin with and without cooling and warming cycles.

| Starting Cisplatin concentration | Concentration of lipids | Cooling & warming cycles | Total concentration of Cisplatin |
|---|---|---|---|
| 0.2 mg/mL | 1.4 mg/mL | No | Not Detectable |
| 0.2 mg/mL | 1.4 mg/mL | Yes | Not Detectable |

TABLE 5-continued

Concentration of cisplatin with and without cooling and warming cycles.

| Starting Cisplatin concentration | Concentration of lipids | Cooling & warming cycles | Total concentration of Cisplatin |
|---|---|---|---|
| 4.0 mg/mL | 28 mg/mL | No | 0.22 mg/mL |
| 4.0 mg/mL | 28 mg/mL | Yes | 0.46 mg/mL |

Example 6

Determination of Captured Volume of Cisplatin Vesicles of the Invention

The object was to determine the nature of the liposomal entrapped cisplatin (HLL cisplatin) by determining the concentration of the entrapped cisplatin within the liposome.

$$V_{total} = V_{liposome} + V_{outside}$$

TABLE 6

[Measurement of $V_{liposome}$]

| | Abs at 450 nm | [dichromate] | $V_{outside}$ | $V_{liposome}$ |
|---|---|---|---|---|
| HLL Cisplatin | 0.874 | 0.67 mg/mL | 1.88 mL | 0.12 mL |
| Saline only | 0.822 | 0.60 mg/mL | 2 mL | 0 mL |

Method: 1) 2 mL HLL Cisplatin prepared as described in Example 4 was concentrated by centrifugation filter kit. 2) 0.8 mL of concentrated sample was recovered and 1.2 mL of 1 mg/mL dichromate was added to recover original volume. 0.8 mL normal saline+1.2 mL of dichromate was also prepared as a control. 3) Abs at 450 nm was measured to detect difference in dichromate concentration. To avoid turbidity from liposome sample, both samples were filtered by centrifugal filtration.

Result: 6% of total volume was occupied by liposomes.

$V_{liposome}$ = 1.53 µL/µmoles lipid (total lipid 39.3 mM)

Next, $V_{liposome} = V_{captured} + V_{bilayer}$

To estimate $V_{bilayer}$, the lamellarity of the vesicles of HLL cisplatin was determined. Measurement of lamellarity of HLL cisplatin vesicles:

| | $F_{total}$ | $F_{inside}$ | % probe lipid at outmost leaflet* |
|---|---|---|---|
| Fluorescence intensity | 14193 | 11349 | 20 |

*% probe lipid at outmost leaflet = $(F_{total} - F_{inside}) \times 100 \div F_{total}$ Method: Cisplatin vesicles were prepared with the method of Example 9, described below (1 liter batch) modified to add 0.5 wt % fluorescence probe lipid (NBD-PE). This probe lipid distributes evenly in membrane inside and outside. The ratio of amount of probes located in outmost membrane layer (surface of liposome) vs. the rest of probes is determined to estimate how many lipid layers exist in HLL Cisplatin. The ratio between probes located on liposome surface and probes located inside liposome was determined by adding a reducing agent dithionite to quench only surface probes. Then, total quenching was achieved by rupturing liposome with detergent.

Result: Outmost bilayer shell contains 40% of total lipids.

Based on geometric calculation, % lipid at outmost bilayer shell would be 52% and 36% for bi-lamellar and tri-lamellar vesicles, respectively. Therefore, it was concluded that the average lamellarity of HLL Cisplatin was three.

Assuming tri-lamellar vesicles, the ratio of $V_{liposome}/V_{captured}$ was calculated to be 1.2635. Therefore, the captured volume was:

$$V_{captured} = V_{liposome} \div 1.2635$$
$$= 1.53\ \mu L/\mu moles\ lipid \div 1.2635$$
$$= 1.21\ \mu L/\mu moles\ lipid$$
$$= 1.21\ \mu L/\mu moles\ lipid \times$$
$$39.3\ mM\ (\text{total lipid concentration})$$
$$= 47.6\ \mu L/Ml$$

The captured volume was 47.6 μL per every mL HLL Cisplatin and 4.76% of total volume. If entrapped cisplatin was assumed to be in an aqueous compartment of liposomes, its local cisplatin concentration would be estimated to be 21.0 mg/mL. This concentration was not only higher than cisplatin solubility limit at room temperature but more significantly it was much higher than initial charging concentration (4 mg/mL).

Example 7

Effect of Cooling Temperature on Entrapment Efficiency of HLL Cisplatin

The object was to find an optimum cooling temperature for the highest entrapment of cisplatin and avoid freezing and thawing. 20 mg/mL DPPC, 8 mg/mL cholesterol, and 4 mg/mL cisplatin suspension was prepared by ethanol infusion. The sample was split to three equal aliquots which were treated by 6 cycles of cooling and warming using three different cooling temperatures. After a treatment of temperature cycles the samples were dialyzed to remove free cisplatin. The resulting data (Table 7) helps optimize the manufacturing process.

TABLE 7

Effect of cooling temperature.

| Post-infusion temperature treatment | Actual temperature of the sample | Cooling and warming cycles | [Cisplatin] mg/mL | % Entrapment |
|---|---|---|---|---|
| Dry ice bath (−70° C.) | frozen | 15 min cold & 15 min warm 6 cycles | 0.34 | 8.5 |

TABLE 7-continued

Effect of cooling temperature.

| Post-infusion temperature treatment | Actual temperature of the sample | Cooling and warming cycles | [Cisplatin] mg/mL | % Entrapment |
|---|---|---|---|---|
| Freezer (−20° C.) | 0° C. | 15 min cold & 15 min warm 6 cycles | 0.98 | 24.5 |
| Ice bath (1° C.) | 4° C. | 15 min cold & 15 min warm 6 cycles | 0.63 | 15.8 |

Example 8

Effect of Number of Temperature Cycles on Entrapment Efficiency

To determine an optimum number of temperature cycles for the most efficient entrapment of cisplatin (Table 8). Samples were prepared as in the previous example. At cooling the temperature of samples was 0° C. The temperature cycle was done by 15 min cooling and 15 min warming. The starting cisplatin concentration was 4 mg/mL and free cisplatin was removed by dialysis.

TABLE 8

Effect of Number of Temperature Cycles.

| | Low Lipids (7.5 mg/mL DPPC & 3 mg/mL cholesterol) | | High Lipids (12.5 mg/mL DPPC & 5 mg/mL cholesterol) | |
|---|---|---|---|---|
| Number of cycles | [cisplatin] | % Entrapment | [cisplatin] | % Entrapment |
| 0 | 0.05 mg/mL | 1.3 | 0.21 mg/mL | 5.3 |
| 1 | 0.11 mg/mL | 2.8 | 0.23 mg/mL | 5.8 |
| 3 | 0.39 mg/mL | 9.8 | 0.88 mg/mL | 22 |

Example 9

Batch Scale and Process Efficiency

To determine if the efficiency of entrapment changed upon changing the size of the batch. The 20 mL batch was prepared as described in example 4. The 1 L batch was prepared indicated in the following steps:
1. Four grams of cisplatin were dissolved in 1 Liter of injection grade 0.9% sodium chloride at 65° C.
2. 20 grams of DPPC and 8 grams of cholesterol were dissolved in 120 mL of absolute ethanol at 65° C.
3. While mixing the cisplatin solution at 300 rpm (65° C.), the lipid solution was metered (infused) into the cisplatin solution at a flow rate of 20 mL/min.
4. After infusion, cisplatin/lipid dispersion was cooled down to −5° C. to 0° C. using a propylene glycol/water bath and kept for 45 minutes (cooling).
5. The dispersion was warmed up to 50° C. and maintained for 15 minutes (warming).
6. The cooling/warming cycle described in steps 4 and 5 was performed for two more times (three cycles total).
7. The dispersion was washed to remove free cisplatin by diafiltration. The permeate removing rate was 17-22 mL/min. The dispersion volume (1 L) was maintained constant by compensating the permeate with a feed of fresh sterile 0.9% sodium chloride solution.

The 200 mL batch was made in the same manner but employed 20% of the components. The process efficiency was defined as the lipid/drug (wt/wt) ratio of initial ingredients divided by the lipid/drug ratio for the final product (Table 9).

TABLE 9

Process efficiency.

| Batch | Batch size | Lipid/drug Pre-formation | Lipid/drug Final product | Process efficiency |
| --- | --- | --- | --- | --- |
| 1 | 20 mL | 4.4 | 54.5 | 0.08 |
| 2 | 200 mL | 5.85 | 27.3 | 0.21 |
| 3 | 200 mL | 5.85 | 37.2 | 0.16 |
| 4 | 200 mL | 5.85 | 36.9 | 0.16 |
| 5 | 1 L | 5.85 | 14.4 | 0.41 |
| 6 | 1 L | 7.0 | 19.2 | 0.36 |
| 7 | 1 L | 7.0 | 21.2 | 0.33 |

Example 10

Stability of Entrapped Lipid-Complexed Cisplatin

Figure 2:
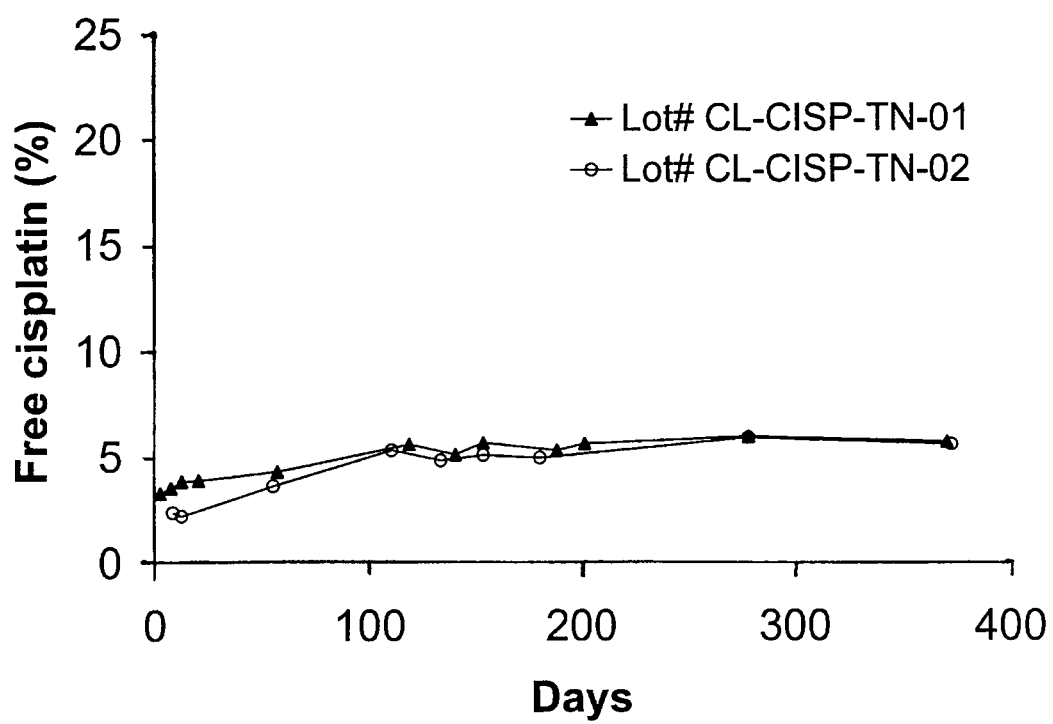
FIG. 2 shows the stability of one liter batches of lipid-complexed cisplatin according to the invention.

The stability of one liter batches of HLL cisplatin was monitored in time for the leakage of internal contents. The resulting data is presented in FIG. 2.

Example 11

Density Characterization of Light and Heavy Fractions

Samples were prepared as in the previous example. At cooling the temperature of samples was 0° C. The temperature cycle was done by 15 min cooling and 15 min warming. The starting cisplatin concentration was 4 mg/mL and free cisplatin was removed by dialysis.

Density Gradient Analysis

Seven different batches of cisplatin lipid complex were used for these experiments. Density gradients were formed using Iodixanol (SIGMA (D1556, lot no. 025K1414)) as a dense media and 0.9% NaCl saline solution to keep osmolality close to normal 300 mOsM. First, about 5.5 mL saline was added to the centrifuge tube, and then the same volume of heavy medium (1:1 mixture of Iodixanol 60% and saline) was layered on the bottom of the tube using a syringe with a long needle. Gradients were formed using a BioComp 107ip Gradient Master at the settings: time=2:14 min, angle=79.0, speed=17 rpm, and using the long tube cap. An aliquot of Cisplatin Lipid Complex samples (1 mL) were placed on the top of the gradient and centrifuged for 30 min at 30,000 rpm at 20° C. After centrifugation, the top 0.8-1.0 mL volume of clear liquid was discarded, and the next 2 mL was collected representing the light fraction. The light fraction is believed to contain liposomes, wherein at least some of the liposomes are associated with cisplatin. There was a detectable amount of free cisplatin in the light fraction of nebulized samples, which was determined by filtering through Centricon-30 filtering devices and subtracted from the total cisplatin.

The rest of the media was removed, leaving only a small yellow pellet on the bottom representing the dense (heavy) fraction, which was subsequently dispersed in 2 mL solution of 75% n-Propanol, 5% saline, 20% water. Cisplatin in the heavy fraction was not completely soluble at this point. An aliquot of this dispersion was taken for cisplatin determination. Another part of the dispersion (1 mL) was mixed with equal volume of 60% n-Propanol and centrifuged 5 min at 1000 rpm on an Eppendorf 5810R centrifuge to settle undissolved cisplatin, and then 1 mL of clear supernatant was used for HPLC lipid determination.

Cisplatin Concentration:

Cisplatin was measured by HPLC by separating cisplatin on YMC-Pack NH2 column using 90% acetonitrile mobile phase and measuring absorbance at 305 nm. Cisplatin standards and samples were diluted in solution of 75% n-Propanol, 5% saline and 20% water. Standards were used with cisplatin concentrations of 75, 50, 25, and 10 µg/mL. Cisplatin peak retention time was usually around 6.4 min.

Lipid Analysis by HPLC.

Lipids were analyzed by HPLC as follows: lipids were separated on a Phenomenex Luna C8(2) column using binary gradient mode. Mobile phase A: methanol 70%, acetonitrile 20%, water 10%, ammonium acetate 0.1%, mobile phase B: methanol 70%, acetonitrile 30%, ammonium acetate 0.07%. Lipid standards and samples were diluted in a solution of 60% n-Propanol, 40% water. Lipids were detected by Sedex 55 Evaporative Light Scattering Detector. The retention time for cholesterol was about 8 mm, for DPPC about 10 min.

Preparation of Samples on Carbon Coated Grids for TEM Analysis

About 50 mL of a cisplatin lipid complex batch was allowed to settle by gravity for at least one week at 4° C. The white to portion containing mostly light fraction was removed and the yellowish brown fraction on the bottom was used for TEM analysis. A small amount of sample (less than 10 microliters) was placed on the carbon coated grid. The grid was placed on the top of a piece of filter paper and spun an Eppendorf centrifuge for 1 minute at 500 RPM to remove excess water. Samples were air-dried for at least one hour before analysis. If centrifugation was done at too low a speed, water was not removed sufficiently enough, and the sample remained too thick, even after drying, tending to boil when exposed to high vacuum inside the TEM microscope. Centrifugation conditions were adjusted to be gentle enough to avoid damage to the grid or loss of the sample. Experimentally, it was found that mild centrifugation at a speed of 200-500×g for 1 min produced samples of good quality with sufficient amount of particles on the grid, but a minimum volume of water.

For comparison, samples of cisplatin crystals (not complexed with a lipid) were prepared by the following procedure: 15 mg cisplatin was dissolved in 5 mL saline solution by heating to 50° C. to provide a 3 mg/mL cisplatin solution. The cisplatin solution was briefly sonicated in a bath of room temperature water. At the first signs of cisplatin precipitation and cloudiness, a small volume was taken with a pipette and immediately placed on a carbon coated grid as described in the preceding paragraph.

Figure 3A:
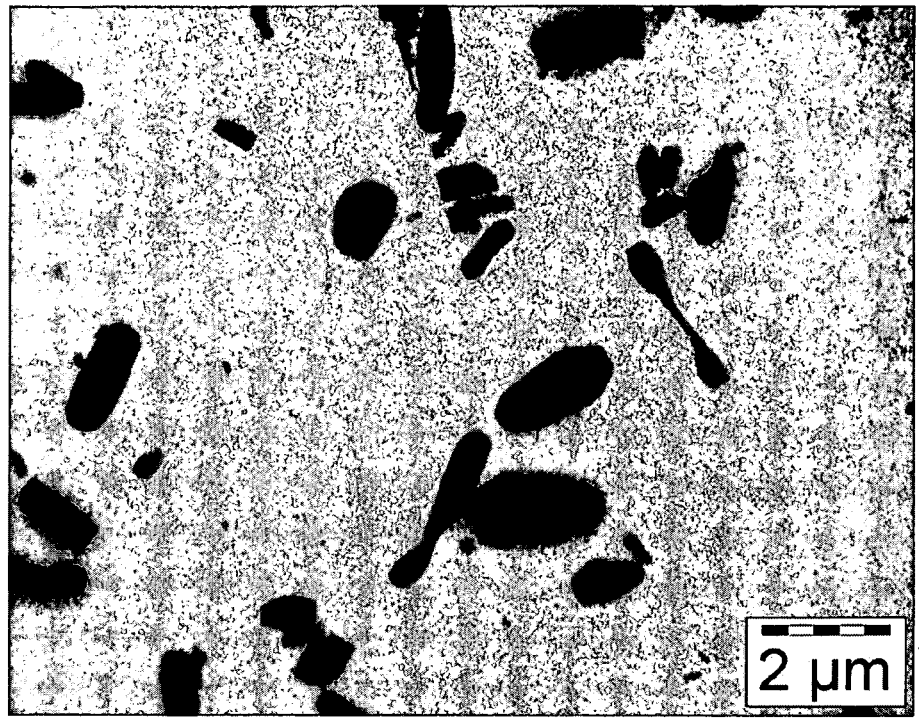
FIGS. 3(A) and 3(B). Cisplatin-rich lipid particulates in the dense, settled fraction of a composition of the present invention. Two representative TEM images are shown (A and B). Samples were prepared as described in the Examples. Large faint circles in the background are part of the copper plate structure.
Figure 3B:
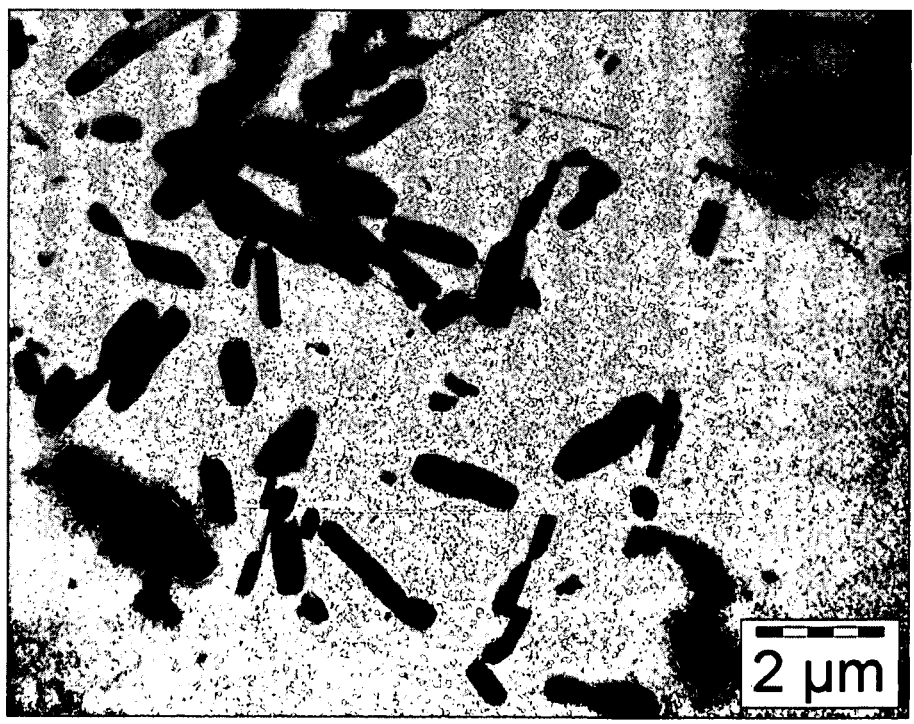

TEM images were obtained on a Zeiss 910 Transmission Electron Microscope at the Princeton Imaging and Analysis Center, Princeton University, Princeton, N.J. An accelerating high voltage of 100 kV was used, and pictures were captured on a charged couple device (CCD) camera at magnifications of 2000 to 25,000×. TEM images of heavy fraction lipid-complexed cisplatin are shown in FIGS. 3A-B. The cisplatin-rich particles were electron dense enough to be seen without staining.

Figure 4A:
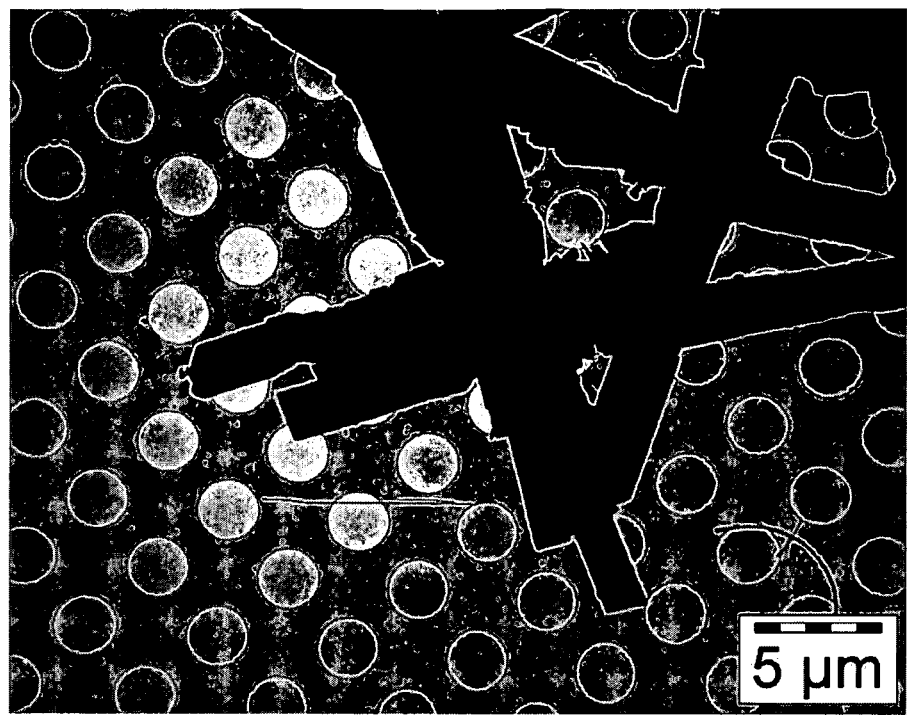
FIGS. 4(A) and (B) are represented TEM images of cisplatin crystals taken at magnification 2000×.
Figure 4B:
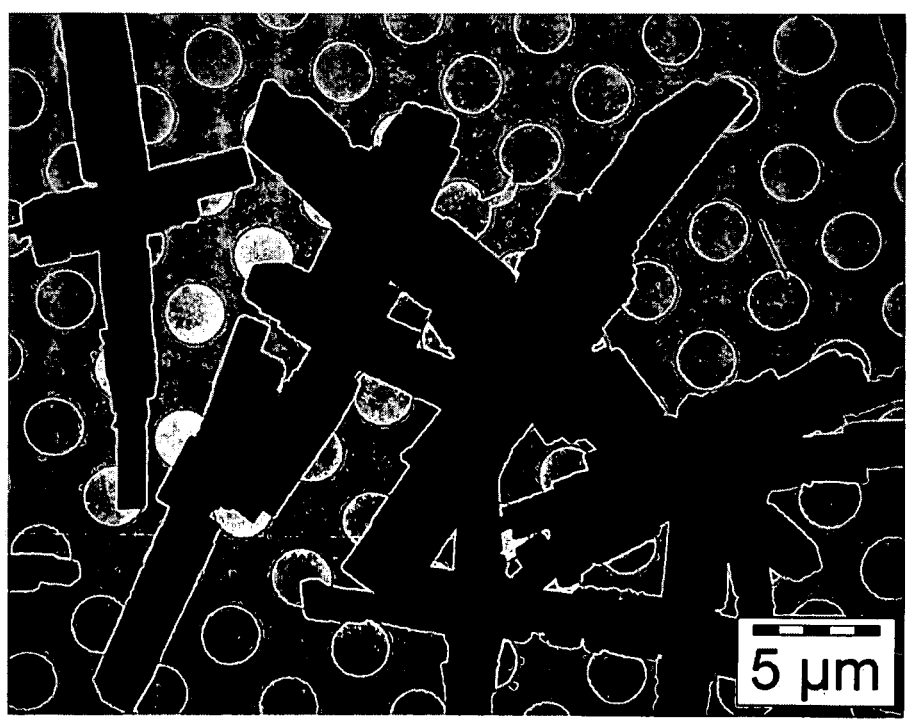

TEM images of cisplatin crystals which are not complexed with a lipid are shown in FIGS. 4A-B. The un-complexed cisplatin crystals appear as dark particles of rectangular shape approximately 2 microns wide and 10-20 microns long. It is believed that the cisplatin particles in the lipid-complexed cisplatin are surrounded by a lipid bilayer, and therefore, cannot grow as large as "free" cisplatin. Additionally, the cisplatin in the lipid-complexed cisplatin does not dissolve in saline upon dilution, further suggesting that the cisplatin is surrounded by a lipid bilayer.

Results

Nine batches of Lipid-cisplatin complex were fractionated on an Iodixanol density gradient as described in the Methods section. All nine samples separated into a similarly positioned white band of light fraction and a yellow pellet of dense fraction. 2 mL of the light fraction were collected and the rest of the liquid was removed. The remaining pellet was dispersed in 2 mL of 75% n-Propanol. Cisplatin and lipid concentrations in each fraction were measured by HPLC as described. The lipid/cisplatin ratio in the dense fraction was very high so that both lipid and cisplatin could not be solubilized in same solvent at high enough concentration for the lipid analysis. For that reason, the lipid-cisplatin mixture in 75% n-propanol solution was centrifuged to remove the insoluble portion of the cisplatin, and the supernatant was used as is for lipid HPLC analysis, as described in Methods.

Results of the density gradient analysis are presented in Table 10. L/D represents the ratio of lipid to cisplatin by weight. The percentages presented are with respect to the total cisplatin or lipid in the formulation. Lower section of the table shows averages of lipid and cisplatin contents in each fraction derived from all nine samples tested. Standard deviations (SD) are shown to demonstrate consistency. These data demonstrate that the majority of lipid (90.6% on average, +/−3.1%) is in the light fraction, while only 0.87+/−0.09% lipid is in the dense fraction. The majority of cisplatin (82.3+/−2.9%) is in the dense fraction, while only 8.4+/−2.1% is in the light fraction. The lipid to drug ratio (L/D) calculated for the total sample was an average of 22.7. The same L/D ratio in separate fractions was as high as 255+/−47 for the light fraction, and as low as 0.24+/−0.03 for dense fraction.

TABLE 10

Distribution of cisplatin and lipids in the light and dense fractions of Cisplatin Lipid Complex samples.

| Batch | Lipid mg/mL | Lipid % total | Cisplatin mg/mL | Cisplatin % total | L/D |
|---|---|---|---|---|---|
| 8 total | 62.2 | | 2.47 | | 25.2 |
| 8 Light fraction | 58.0 | 93.3 | 0.20 | 8.2 | 285 |
| 8 Dense fraction | 0.49 | 0.79 | 2.01 | 81.3 | 0.24 |
| 9 total | 51.5 | | 2.46 | | 20.9 |
| 9 Light fraction | 47.8 | 92.7 | 0.18 | 7.2 | 270 |
| 9 Dense fraction | 0.44 | 0.85 | 1.96 | 79.7 | 0.22 |
| 10 total | 55.2 | | 2.57 | | 21.5 |
| 10 Light fraction | 46.7 | 84.7 | 0.20 | 7.7 | 237 |
| 10 Dense fraction | 0.47 | 0.85 | 2.15 | 83.6 | 0.22 |
| 11 total | 57.3 | | 2.61 | | 22.0 |
| 11 Light fraction | 49.7 | 86.8 | 0.15 | 5.9 | 326 |
| 11 Dense fraction | 0.48 | 0.84 | 2.20 | 84.2 | 0.22 |
| 12 total | 57.9 | | 2.57 | | 22.5 |
| 12 Light fraction | 51.6 | 89.1 | 0.18 | 6.9 | 290 |
| 12 Dense fraction | 0.47 | 0.82 | 2.17 | 84.3 | 0.22 |
| 13 total | 80.46 | | 3.36 | | 24.0 |
| 13 Light fraction | 73.42 | 91.26 | 0.44 | 13.0 | 168 |
| 13 Dense fraction | 0.82 | 1.01 | 2.58 | 76.7 | 0.32 |
| 14 total | 71.19 | | 3.41 | | 20.9 |
| 14 Light fraction | 64.82 | 91.06 | 0.29 | 8.7 | 220 |
| 14 Dense fraction | 0.65 | 0.92 | 2.76 | 81.1 | 0.24 |
| 15 total | 66.92 | | 2.83 | | 23.7 |
| 15 Light fraction | 62.35 | 93.17 | 0.23 | 8.0 | 275 |
| 15 Dense fraction | 0.66 | 0.99 | 2.45 | 86.5 | 0.27 |
| 16 total | 68.5 | | 2.86 | | 23.9 |
| 16 Light fraction | 64.0 | 93.48 | 0.28 | 9.8 | 228 |
| 16 Dense fraction | 0.51 | 0.75 | 2.40 | 83.8 | 0.21 |
| Average | | | | | 22.7 |
| Light fraction | | 90.6 | | 8.4 | 255 |
| +/−SD | | 3.1 | | 2.1 | 47 |
| Dense fraction | | 0.87 | | 82.3 | 0.24 |
| +/−SD | | 0.09 | | 2.9 | 0.03 |

Example 12

Nebulization Study

Separation of Light and Dense Fractions 30 mL of cisplatin lipid complex was mixed with 10 mL iodixanol 30% in saline. This mixture was in half and 20 mL portions were layered on the top of another 10 mL iodixanol 30% in saline using two 50 mL centrifuge tubes. The samples were centrifuged for 30 minutes at 4000 rpm at 5° C. on an Eppendorf 5810 centrifuge. Supernatant, containing a mixture of light and heavy fractions, was discarded. The pellet, containing the dense fraction of the cisplatin lipid composition, was gently dispersed in 5 mL of saline. After determining the concentration of cisplatin, the concentration was adjusted to make the concentration 2.7 mg/mL of cisplatin.

To obtain the light fraction, the cisplatin lipid complex batch was allowed to settle by gravity at 5° C. for 1 week. The top portion of the sample, containing the light fraction, was collected.

Nebulization Studies

Figure 5A:
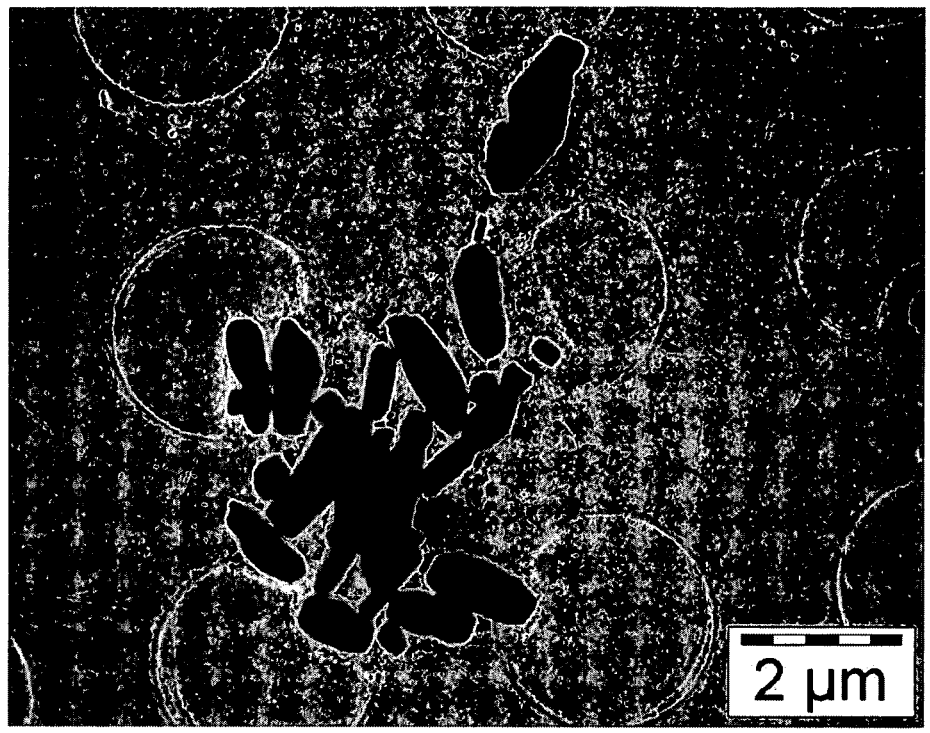
FIGS. 5(A) and 5(B) are Representative TEM images of the dense fraction particles from the density gradient of a nebulized cisplatin lipid complex formulation. Images were taken at magnification 6300× (A) and 8000× (B).
Figure 5B:
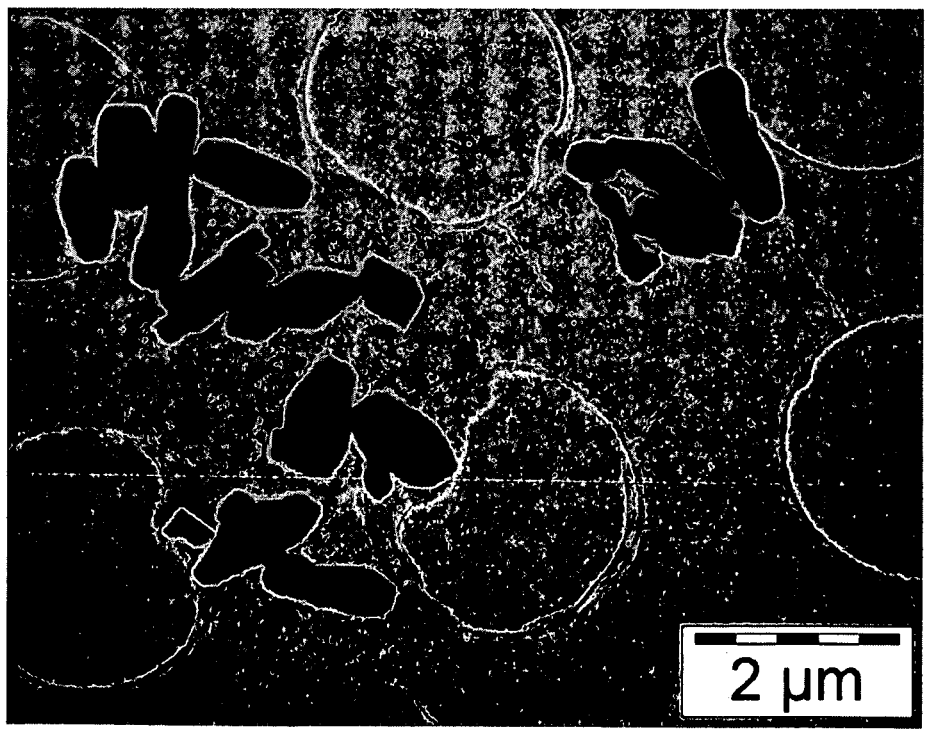
Figure 6A:
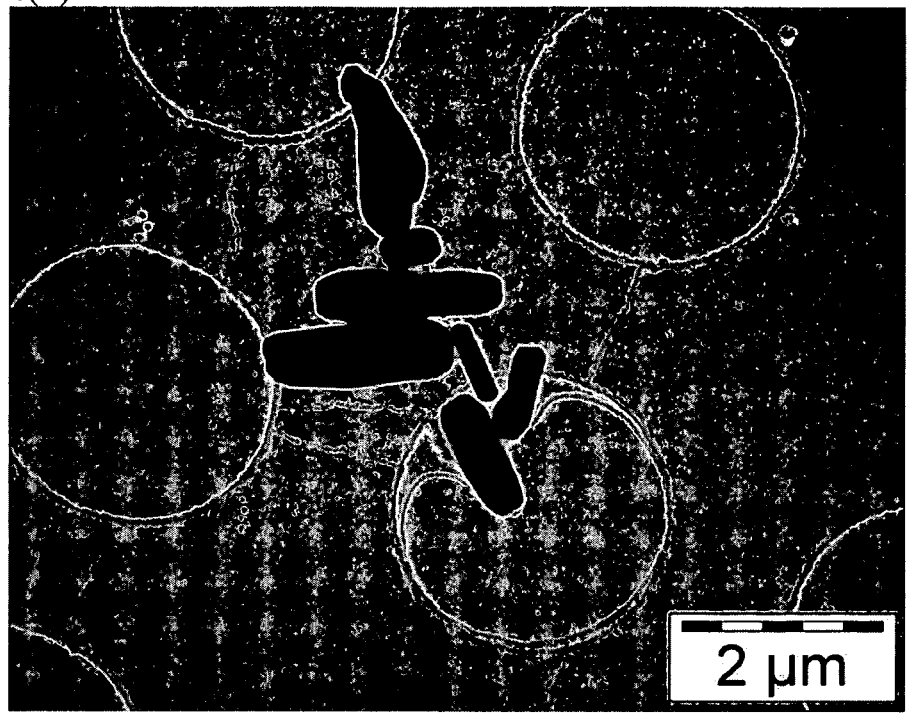
FIGS. 6(A) and (B) are representative TEM images of the dense fraction particles from the density gradient of a nebulized cisplatin lipid complex formulation. Images were taken at magnification 8000× (A) and 4000× (B).
Figure 6B:
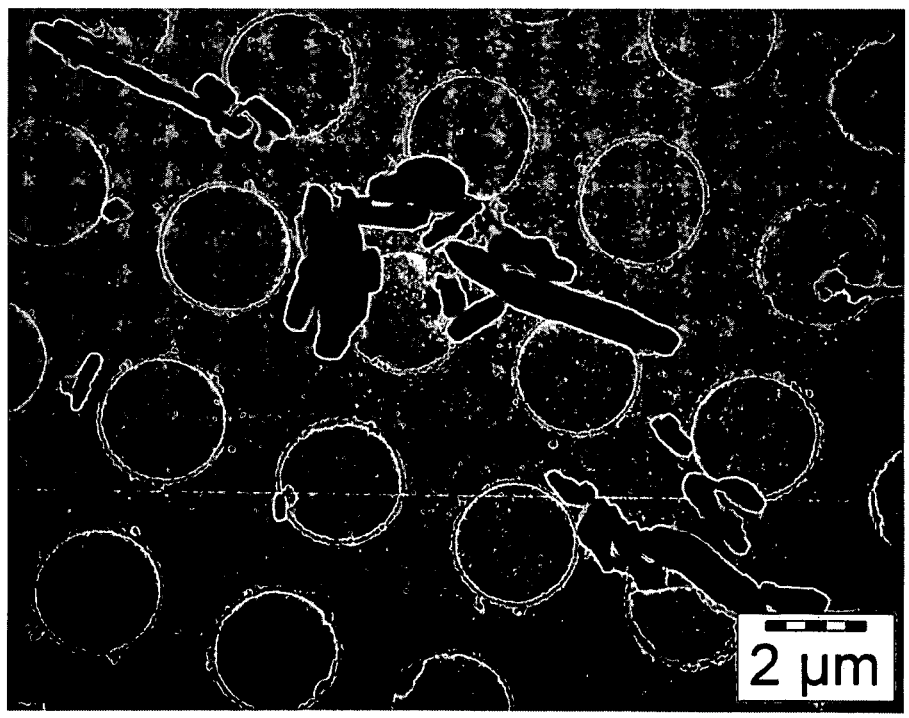
Figure 8A:
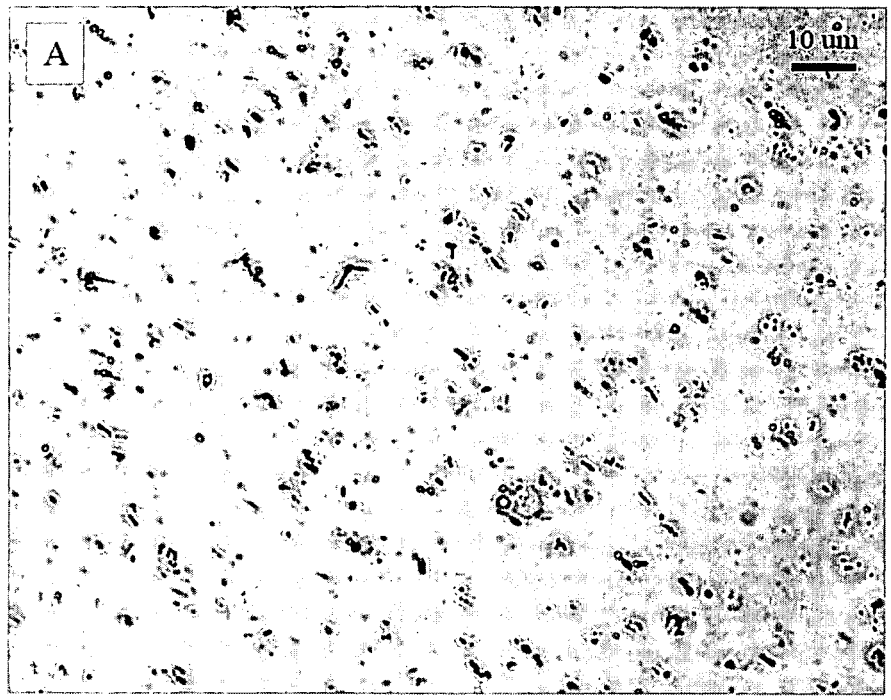
FIGS. 8(A)-(D) are representative optical micrographs of a composition of the present invention.
Figure 8B:
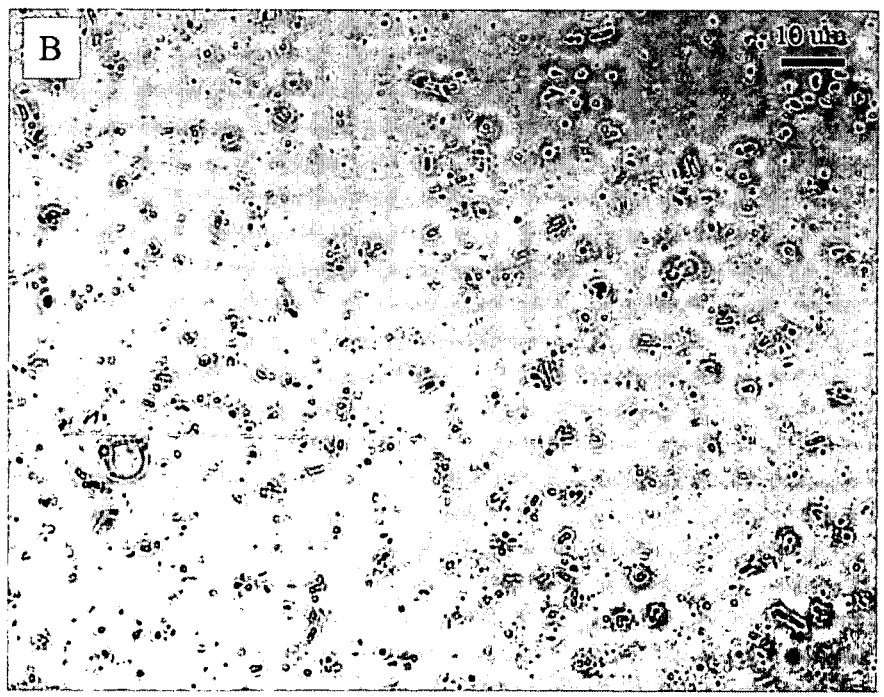
Figure 8C:
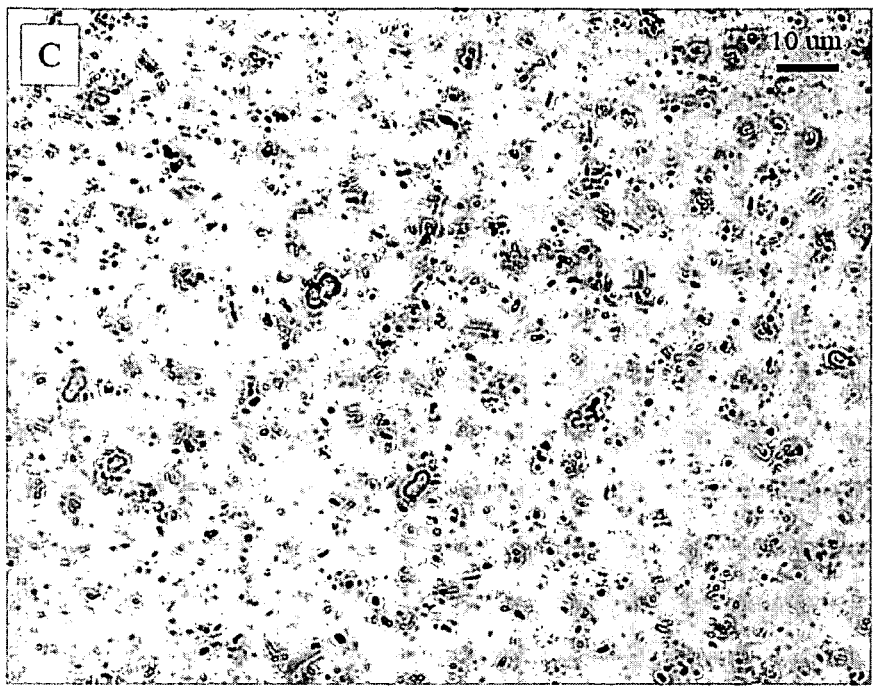
Figure 8D:
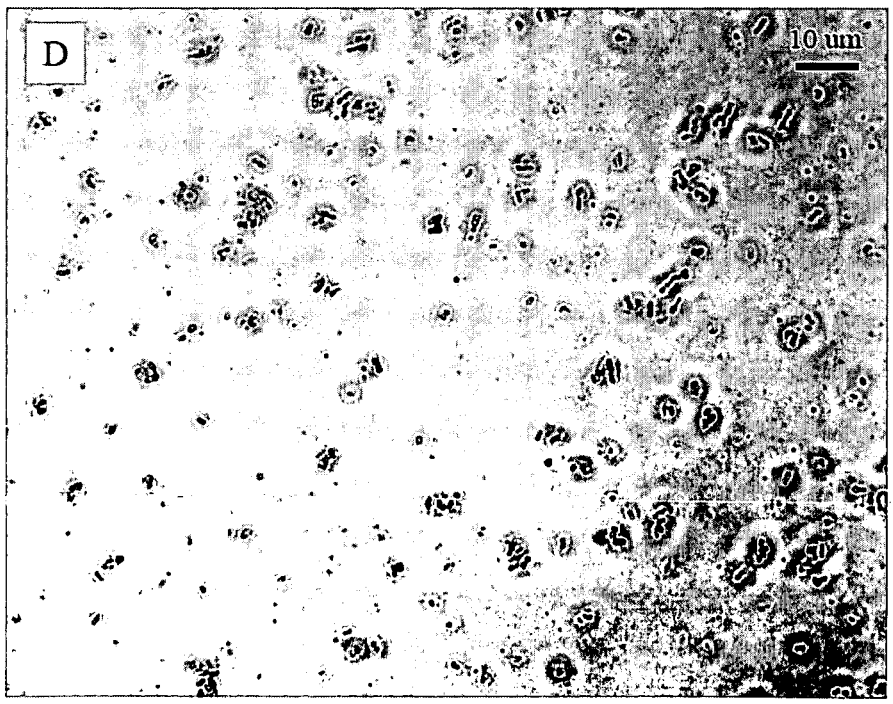
Figure 9A:
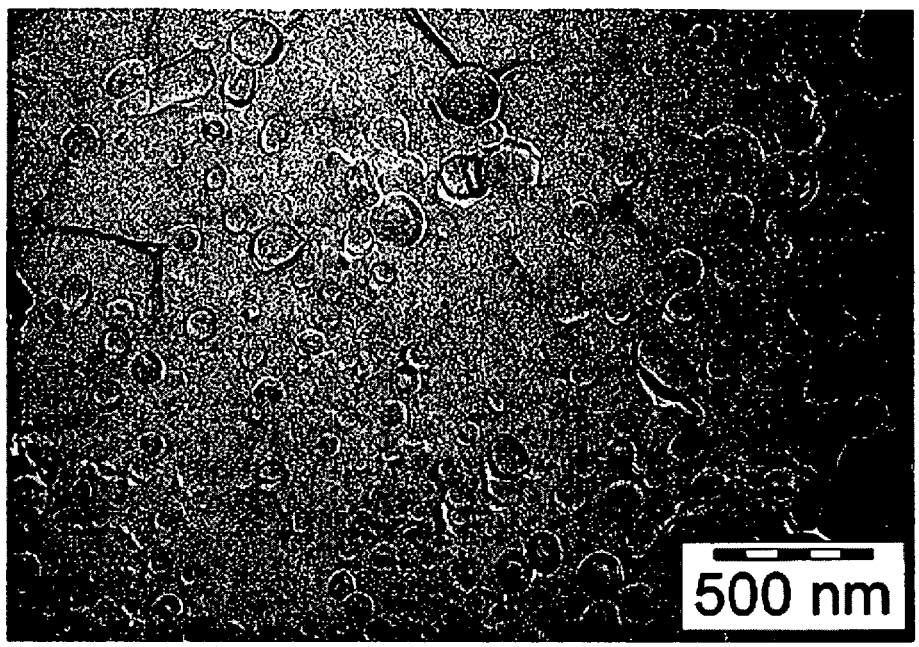
FIGS. 9(A) and (B) are representative freeze fracture electron micrographs of a composition of the present invention.
Figure 9B:
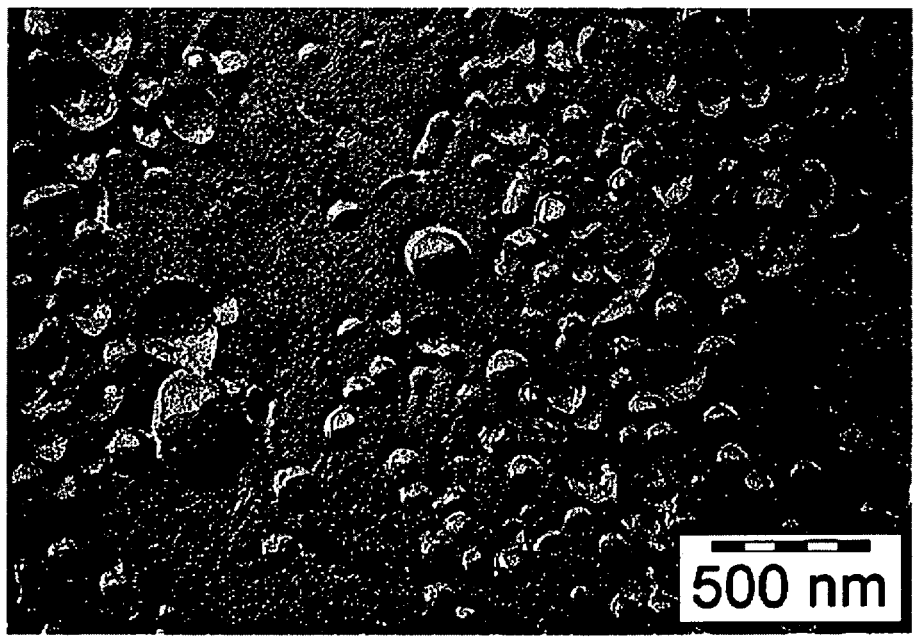
Figure 10A:
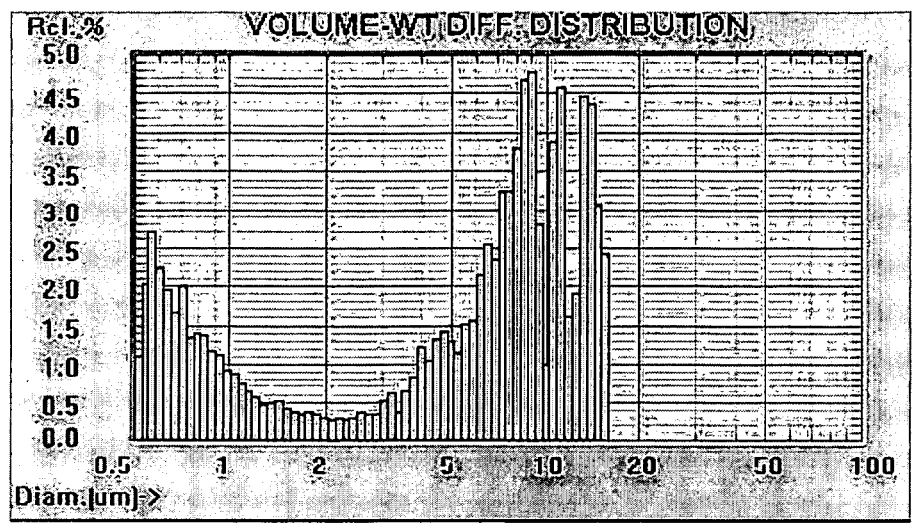
FIGS. 10(A)-(D) are graphs depicting the particle size analysis of several batches of a composition of the present invention.
Figure 10B:
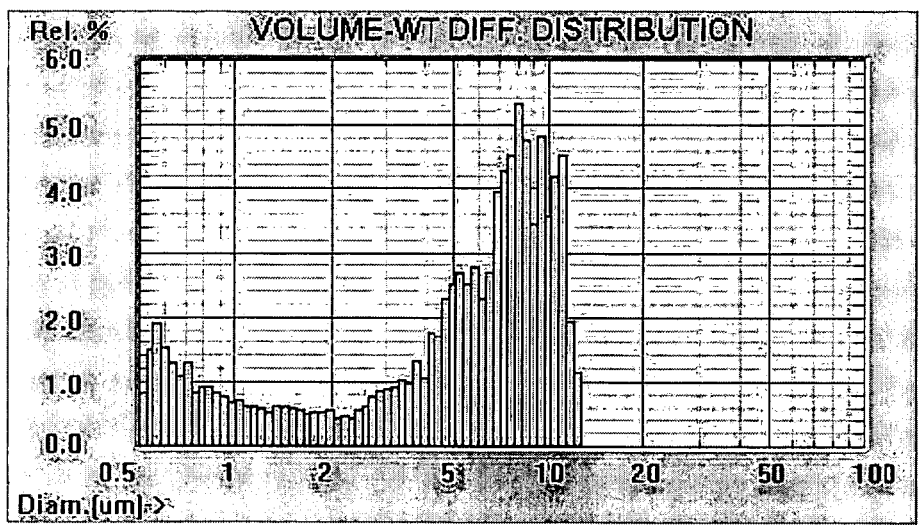
Figure 10C:
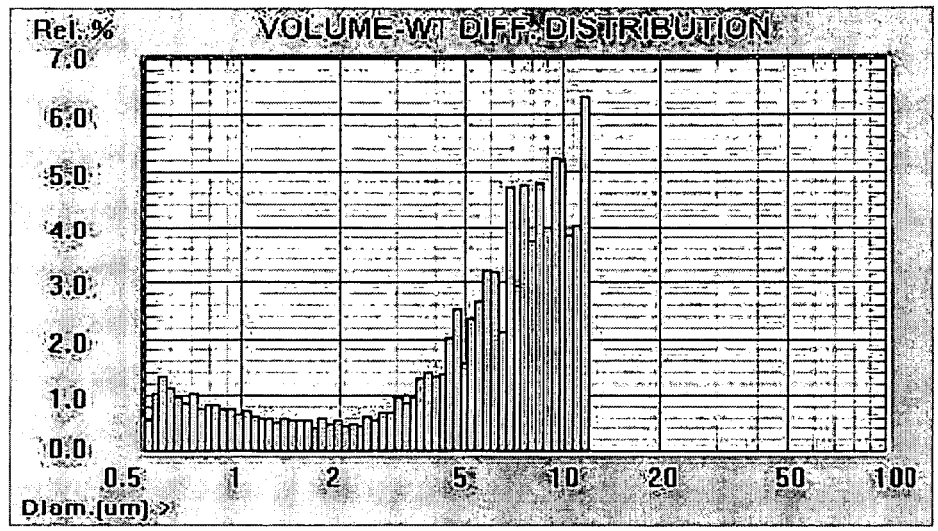
Figure 10D:
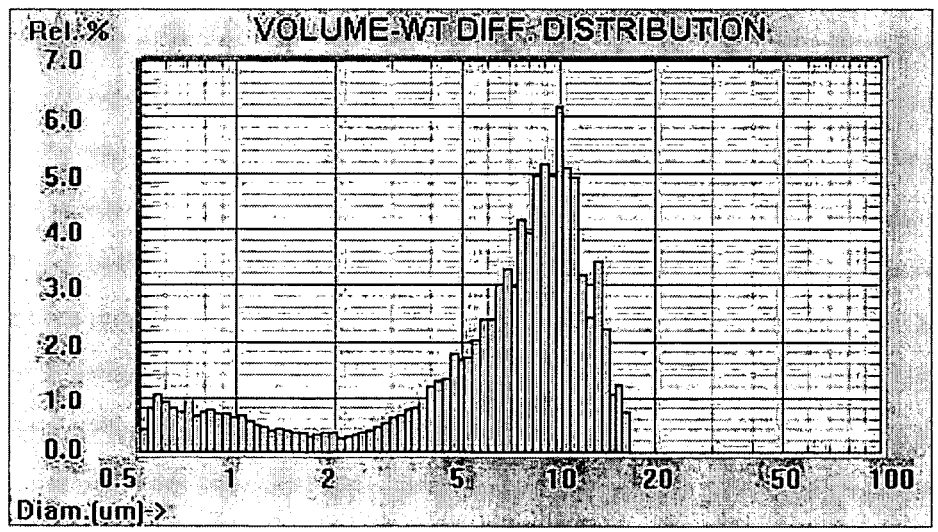

TEM Analysis of Nebulized Lipid-Complexed Cisplatin:

5 mL of sample was nebulized using a PARI-LC STAR nebulizer, and the aerosol was collected by a chilled (ice water) impinger. From the impinger, 2.5 mL of the nebulizate was obtained for the analysis. An aliquot of the nebulizate was filter-centrifuged using a centricon-YM-30, when necessary, immediately after nebulization to determine non-encapsulated (free) cisplatin. Nebulization air pressure was 30 PSI and the flow rate of the aerosol collection system provided by the pump was 8 L/min. 1 mL of aerosol, collected in an impinger, was diluted with 2 mL of saline and allowed to incubate at 4° C. for 20 hours. In parallel, 1 mL of the original (non-nebulized) formulation was treated the same. After the heavy fraction settled, the whiter top portion of each sample was removed and the yellowish portion was dispersed in a solution of 10% iodixanol in saline. Samples were centrifuged at 4000 RPM for 20 minutes on an Eppendorf 5810 centrifuge. Supernatants were discarded and pellets having heavy fraction particles dispersed in 200 microliters saline each. the amount of heavy fraction pellet obtained from the nebulized formulation was less than the amount from the original formulation. Samples for TEM were prepared as described previously. FIG. 5 depicts TEM images of the nebulized heavy fraction particles and FIG. 6A-B depicts TEM images of the non-nebulized heavy fraction particles. In both cases, the particles are dark and dense of rectangular and rhomboidal shape of average size between 1 and 2 microns. In some instances, bigger and longer particles of 3 microns and greater in size were present in the non-nebulized sample (FIG. 8B) compared to the nebulized sample.

Density Gradient Analysis of Nebulized Lipid-Complexed Cisplatin:

5 mL of sample was nebulized as described above. Within a few hours after nebulization, a 1 mL sample was run on the density gradient system. Visibly all the gradients appeared similar to the ones of the original samples (non-nebulized). Each fraction was collected as described above and analyzed for lipid and cisplatin content.

The results of density gradient analysis of the samples after nebulization are presented in Table 11. Similar to the non-nebulized samples, the majority of lipid (85.2% on average, =/−6.1%) was found in the light fraction, while only 0.36%+/−0.08% lipid was in the dense fraction. The distribution of cisplatin was 46.0+/−1.2% in the dense fraction, and 8.5+/−1.1% in the light fraction. The L/D ratio was similar to that in the non-nebulized samples, being 232+/−15 for the light fraction, and 0.18+/−0.03 for the dense fraction.

TABLE 11

Density Gradient Analysis After Nebulization.

| Batch | Lipid mg/mL | Lipid % total | Cisplatin mg/mL | Cisplatin % total | L/D |
|---|---|---|---|---|---|
| 11 total | 70.1 | | 3.22 | | 21.8 |
| 11 Light fraction | 55.8 | 79.7 | 0.25 | 7.7 | 225 |
| 11 Dense fraction | 0.28 | 0.40 | 1.50 | 46.5 | 0.19 |
| 12 total | 61.9 | | 2.80 | | 22.1 |
| 12 Light fraction | 56.8 | 91.7 | 0.23 | 8.1 | 249 |
| 12 Dense fraction | 0.25 | 0.4 | 1.25 | 44.6 | 0.20 |
| 13 total | 77.57 | | 2.80 | | 23.76 |
| 13 Light fraction | 60.98 | 78.61 | 0.23 | 9.6 | 195.15 |
| 13 Dense fraction | 0.33 | 0.43 | 1.25 | 44.6 | 0.23 |
| 14 total | 71.65 | | 3.17 | | 22.59 |
| 14 Light fraction | 63.46 | 88.56 | 0.28 | 8.9 | 225.85 |
| 14 Dense fraction | 0.26 | 0.37 | 1.40 | 44.2 | 0.19 |
| 16 total | 77.2 | | 3.00 | | 25.7 |
| 16 Light fraction | 64.9 | 84.1 | 0.29 | 9.8 | 221 |
| 16 Dense fraction | 0.21 | 0.27 | 1.40 | 46.8 | 0.15 |
| Average | | | | | 23.2 |
| Light fraction | | 84.5 | | 8.8 | 223 |
| +/−SD | | 5.6 | | 0.9 | 15 |
| Dense fraction | | 0.37 | | 45.3 | 0.19 |
| +/−SD | | 0.06 | | 1.2 | 0.03 |

A comparison of density gradient analyses before and after nebulization is shown in Table 12.

TABLE 12

Pre and post nebulization gradient analysis.

| Cisplatin Lipid Complex | Cisplatin % of total | | | Lipid/Drug ratio | | |
|---|---|---|---|---|---|---|
| Fractions | PreNeb | PostNeb | Change | PreNeb | PostNeb | Change |
| Light fraction | 8.4 | 8.8 | 0.4 | 255 | 223 | −32 |
| SD | 2.1 | 0.9 | 3.0 | 47 | 15 | 52 |
| Dense fraction | 82.3 | 45.3 | −37.0 | 0.24 | 0.19 | −0.05 |
| SD | 2.9 | 1.2 | 4.1 | 0.03 | 0.03 | .06 |

Figure 7:
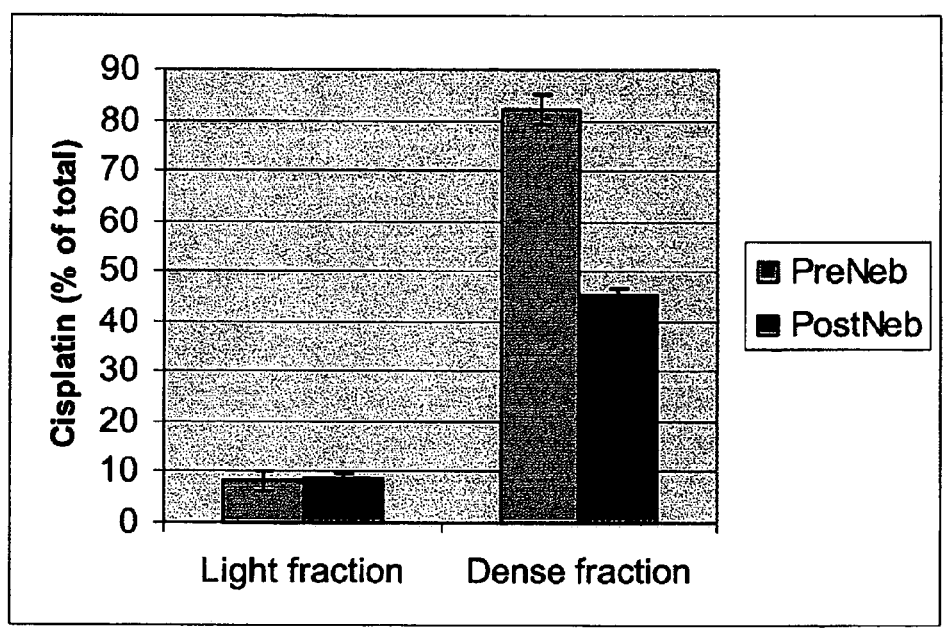
FIG. 7 depicts a bar graph showing the effect of nebulization on the distribution of cisplatin in the light and dense fractions of a composition of the present invention.

FIG. 7 shows a bar graph of the effect of nebulization on the distribution of cisplatin in the light and dense fractions of the cisplatin lipid complex. While not being bound by any particular theory, the above data indicates that a significant portion of cisplatin leaks out of the dense fraction during nebulization, but does not leak out of the light fraction to a significant extent.

The separated light and dense fractions were nebulized as described above and then analyzed for total and free cisplatin. Table 13 shows the results, compared with nebulization of the total cisplatin lipid complex. The total cisplatin lipid complex sample lost 45.1% of encapsulated cisplatin during nebulization. The light fraction was essentially unchanged. The dense fraction lost more than 70% of its original encapsulated cisplatin. The results demonstrate that the dense fraction leaks, while the light fraction essentially does not. Additionally, the dense fraction leaked to a greater extent when nebulized alone, compared to the total cisplatin lipid complex sample. While not being bound by any particular, it is believed that liposomes contained in the light fraction "protect" the dense particles during nebulization, thereby reducing cisplatin leakage.

TABLE 13

| Cisplatin Lipid Complex fractions | Cisplatin free % preNeb | Cisplatin free % postNeb | Leakage % |
|---|---|---|---|
| Total | 4.4 | 49.5 | 45.1 |
| Light fraction | 65.7 | 64.7 | −1.0 |
| Dense fraction | 3.1 | 74.7 | 71.6 |

The distribution of cisplatin in a the light and dense fractions are shown in FIG. 7.

Example 13

Comparison of Cisplatin and Transplatin Entrapment

Entrapment of cisplatin or transplatin in a lipid complex by repetitive cooling/heating achieves a high drug/lipid ratio as shown in Table 14.

TABLE 14

| | cisplatin | transplatin |
|---|---|---|
| Starting drug concentration | 5 mg/mL | 1 mg/mL |
| Lipids (DPPC:Cholesterol = 7:3 wt) | 25 mg/mL | 5 mg/mL |
| Temperature cycles | 6 cycles | 6 cycles |
| Final drug concentration | 1.4 mg/mL (1.4% free) | 0.3 mg/mL (6.0% free) |
| Recovery % | 29% | 26% |
| Drug/Lipid | 0.056 | 0.06 |

Example 14

Optical Microscopy

Four batches of the formulation were studied by optical microscopy. Batches 17-20 are shown in FIGS. 8A-D, respectively. The optical micrographs depict round particles of about 1 to 2 microns in size, or less, and a number of rod-shaped particles of about 1-2 microns wide and up to about 10 microns in length.

Example 14

Freeze Fracture Images

An aliquot of the sample was plated on a copper plate and then sandwiched with another copper plate. This sample sandwich was quickly frozen by dipping into liquid propane and transferred to a copper plate holder, which was immersed in liquid nitrogen. The holder was transferred into a vacuum-freeze chamber (Balzers freeze-etching system BAF 400 T), which was at a temperature of 170° C. with a vacuum of $2\text{-}5\times10^{-6}$ bar. Fracturing and subsequent Pt and carbon coating were carried out at −115° C. The replica was taken out of the chamber and treated with 2% nitric acid for about 4-5 hours, followed by bleaching overnight. The washed replica was placed on a copper grid for EM observation. Representative freeze fracture images are shown in Figure Example 16

Particle Size Analysis

Samples of the heavy fraction comprising lipid-complexed cisplatin were diluted in filtered saline (NaCl 0.9%) at a ratio of 1:2000 and analyzed by an AccuSizer Optical Particle Sizer 780 using the following settings: injection loop volume 1 mL, Data collection time 60 s, Detector LE 400-05SE summary mode, Minimum diameter 0.05 microns. The detector used counts only particles 0.5 microns and larger. Four batches were analyzed (batch nos. 17-20), as shown in FIGS. 10A-D. The distribution plots show relative volumes occupied by particles of different sizes. The particles in the range of 0.5 to 1 micron represent the right side tail of the main distribution of the light fraction, the majority of which has particle sizes less than 5 microns. The plots also show a large peak at the right from 1 micron to 20 micron, with a median size of about 8 to 10 microns.

Figure 11A:
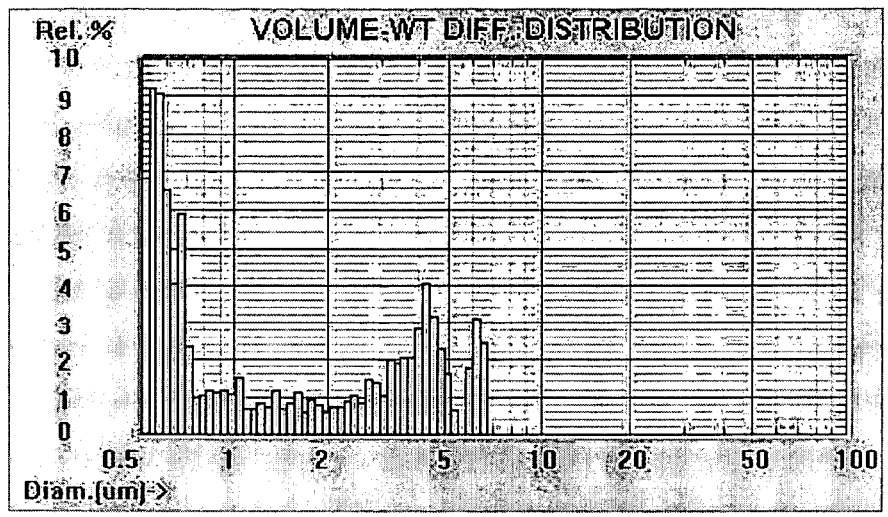
FIGS. 11(A) and (B) are graphs depicting the particle size analysis of two batches of a composition of the present invention after nebulization.
Figure 11B:
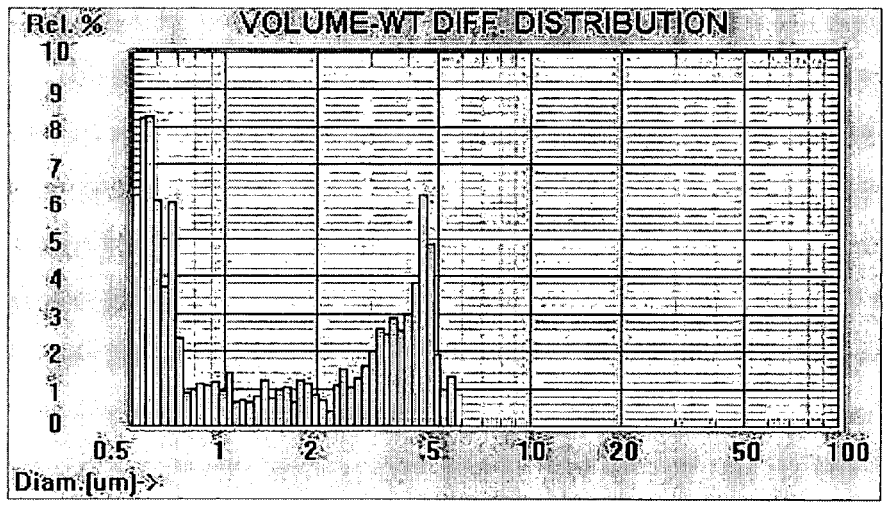

Batches 17 and 20 were subjected to particle size analysis after nebulization as well, and the results are shown in FIGS. 11A-B.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A lipid-complexed active platinum compound aggregate comprising a therapeutic amount of an active platinum compound and a lipid component,
    wherein the lipid component consists of cholesterol and dipalmitoylphosphatidylcholine (DPPC),
    and the lipid to active platinum compound ratio (L/D) by weight of the aggregate is 0.1 (L/D) to 1 (L/D).

2. The lipid-complexed active platinum compound aggregate of claim 1, wherein the ratio of DPPC to cholesterol is about 1:1 to about 5:−1 by weight.

3. The lipid-complexed active platinum compound aggregate of claim 2, wherein the ratio of DPPC to cholesterol is about 2:1 to about 4:1 by weight.

4. The lipid-complexed active platinum compound aggregate of claim 3, wherein the ratio of DPPC to cholesterol is about 2.25:−1 by weight.

5. A pharmaceutical formulation comprising the lipid-complexed active platinum compound aggregate of claim 1, and a pharmaceutically acceptable carrier or diluent.

6. The pharmaceutical formulation of claim 5, wherein the formulation is formulated for administration by inhalation by a patient.

7. The pharmaceutical formulation of claim 6, wherein the formulation is formulated for administration by injection into a patient.

8. The lipid-complexed active platinum compound aggregate of claim 1, wherein the lipid to active platinum compound ratio (L/D) by weight of the lipid-complexed cisplatin aggregate is 0.10 (L/D) to 0.50 (L/D).

9. The lipid-complexed active platinum compound aggregate of claim 1, wherein the lipid to active platinum compound ratio (L/D) by weight is 0.15 (L/D) to 0.45 (L/D).

10. The lipid-complexed active platinum compound aggregate of claim 1, wherein the lipid to active platinum compound ratio (L/D) by weight is 0.20 (L/D) to 0.40 (L/D).

11. The lipid-complexed active platinum compound aggregate of claim 1, wherein the lipid to active platinum compound ratio (L/D) by weight is 0.20 (L/D).

12. The composition of claim 1, wherein the lipid-complexed active platinum compound aggregate comprises about 75% to about 99% of the total active platinum compound in the composition.

13. The lipid-complexed active platinum compound aggregate of claim 1, wherein the active platinum compound is selected from the group consisting of cisplatin, carboplatin, oxaliplatin, iproplatin, tetraplatin, transplatin, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)) and JM335 (trans-amminedichloro(cyclohexylamine)dihydroxoplatinum(IV)).

14. The lipid-complexed active platinum compound aggregate of claim 13, wherein the active platinum compound is cisplatin.

15. The lipid-complexed active platinum compound aggregate of claim 14, wherein the lipid to cisplatin ratio (L/D) by weight is 0.15 (L/D) to 0.45 (L/D).

16. The lipid-complexed active platinum compound aggregate of claim 14, wherein the lipid to cisplatin ratio (L/D) by weight is 0.20 (L/D) to 0.40 (L/D).

17. The lipid-complexed active platinum compound aggregate of claim 14, wherein the lipid to cisplatin ratio (L/D) by weight is 0.20 (L/D).

* * * * *